United States Patent
Dougherty et al.

(10) Patent No.: US 12,048,653 B2
(45) Date of Patent: Jul. 30, 2024

(54) PATIENT PROTECTION APPARATUS AND ASSOCIATED METHODS

(71) Applicants: Natalia Valderrama Dougherty, Melbourne, FL (US); Bryan Dougherty, Melbourne, FL (US)

(72) Inventors: Natalia Valderrama Dougherty, Melbourne, FL (US); Bryan Dougherty, Melbourne, FL (US)

(*) Notice: Subject to any disclaimer, the term of this patent is extended or adjusted under 35 U.S.C. 154(b) by 771 days.

(21) Appl. No.: 17/236,015

(22) Filed: Apr. 21, 2021

(65) Prior Publication Data
US 2021/0244594 A1 Aug. 12, 2021

Related U.S. Application Data

(60) Provisional application No. 63/022,447, filed on May 9, 2020.

(51) Int. Cl.
*A61G 10/00* (2006.01)
*A61C 19/00* (2006.01)

(52) U.S. Cl.
CPC ............ *A61G 10/005* (2013.01); *A61C 19/00* (2013.01)

(58) Field of Classification Search
CPC .... A61M 21/0094; A62B 29/00; A62B 31/00; A61B 90/05; A61B 90/40; A61B 2090/401
See application file for complete search history.

(56) References Cited

U.S. PATENT DOCUMENTS

| | | | |
|---|---|---|---|
| 6,302,109 B1 * | 10/2001 | Parnes | A61B 46/00 128/845 |
| 2021/0307871 A1 * | 10/2021 | Edalati | A61G 10/02 |
| 2021/0307985 A1 * | 10/2021 | Staab | A61G 10/005 |
| 2021/0338361 A1 * | 11/2021 | Majzoub | A61B 46/20 |

FOREIGN PATENT DOCUMENTS

IT 202000010318 A1 * 8/2020

* cited by examiner

*Primary Examiner* — Thaddeus B Cox
(74) *Attorney, Agent, or Firm* — Bullock Law; Stephen Bullock

(57) ABSTRACT

Embodiments of the present invention are related to a patient protection apparatus with a first side, a second side, a back, a top and a front visor. The first side and second side each include at least one of a side arm aperture, an instrument aperture and an air filter interface. The back includes a plurality of back arm apertures and at least one back instrument aperture. The top has a wider length at the front of the apparatus and a shorter length at the back allowing the first side and second side to taper at an angle from the front to the back. Some embodiments include wheels for easy transportation and removable front enclosures. Other embodiments include smaller dimensions for ease of transport and more versatile application.

20 Claims, 18 Drawing Sheets

PATIENT PROTECTION APPARATUS AND ASSOCIATED METHODS

RELATED APPLICATIONS

This application claims the benefit under 35 U.S.C. § 119(e) of U.S. Provisional Patent Application Ser. No. 63/022,447 titled Patient Protection Apparatus and Associated Methods filed on May 9, 2020, the entire contents of which are incorporated herein by reference.

FIELD OF THE INVENTION

The present invention relates to systems and methods for protecting patients during procedures. In particular, the present invention relates to a patient protection apparatus and associated methods.

BACKGROUND

In early 2020, the world was plagued by the coronavirus pandemic causing widespread COVID-19 illness and loss of human life. As a result, the U.S. economy sharply declined and for a period of time most economic and social activity was halted. It has been determined that the coronavirus, like many other harmful microorganisms, is spread when people are in close proximity to each other.

The coronavirus greatly impacted professional services such as medical and dental assistance. Not only were services curtailed, but some were prohibited altogether. Studies have shown that the use of dental services in particular fell 75% in March 2020 and 79% in April 2020 compared to a year earlier. The decline in available dental services during the pandemic caused a shift in the medical industry leaving more patients seeking emergency room attention for dental procedures otherwise handled by local dental professionals. This paradigm shift in treatment not only disrupted the level of dental care provided to patients, but diverted resources from hospitals needed to fight the coronavirus itself.

For dentists, commonly used dental equipment that create aerosols and possible airborne contamination include ultrasonic scalers, high-speed dental handpieces, air and water syringes, and air polishers. These procedures and tools are an integral part of the dental profession and a cornerstone of a healthy modern society.

There exists a need in the art for an apparatus that allows caretakers to safely perform standard medical and dental procedures that protects both the patient and the caretaker. There exists a need in the art for a patient protection apparatus and associated methods.

This background is provided to reveal information believed by the applicant to be of possible relevance to the present invention. No admission is made as to prior art and nothing within the background should be construed as prior art against the present invention.

SUMMARY OF THE INVENTION

Embodiments of the present invention are related to a patient protection apparatus with a first side, a second side, a back, a top and a front visor. The first side and second side may each include at least one of a side arm aperture, an instrument aperture and an air filter interface. The back may include a plurality of back arm apertures and at least one back instrument aperture. The top may have a wider length at the front of the apparatus and a shorter length at the back allowing the first side and second side to taper at an angle from the front to the back.

The first side, second side, back, top and front visor may be structured to create a hollow interior that tapers from front to back. At least one of the first side, second side, back, top and front visor may be transparent. The first side and second side may extend from a height proximate ground level to a height structured to accommodate a standard patient platform with patient at one of a horizontal and upwardly angled position. The side arm apertures and back arm apertures may be located within an upper third of the patient platform apparatus.

Each respective side and back combination may be structured to accommodate a caretaker administering patient services utilizing one side arm aperture and one back arm aperture. Additionally, the plurality of back arm apertures may be structured to accommodate a caretaker administering patient services utilizing two back arm apertures. Furthermore, the apparatus may be structured to accommodate a single caretaker utilizing a side arm aperture and back arm aperture simultaneously or two back arm apertures simultaneously. The apparatus may also be structured to accommodate a plurality of caretakers utilizing at least one respective side arm aperture and one respective back arm aperture simultaneously.

This embodiment may further include a front enclosure removably engaged to a plurality of top attachment members and side attachment members. The front enclosure my be structured to extend downward from the top to a patient lap edge. The front enclosure may include a pair of enclosure overhangs structured to extend downward and around a patient platform.

The apparatus may further include a removably engaged tinted shield. The tinted shield may be removably engaged via at least one of top pegs fixedly attached to the apparatus top structured to accommodate corresponding holes in the tinted shield, hook and loop fasteners on the apparatus and the tinted shield, and oppositely charged magnets fixedly attached to the tinted shield and the apparatus.

This embodiment of the apparatus may further include a removably attached bottom front enclosure extending from the first side across the front of the apparatus to the second side of the apparatus. The bottom front enclosure may removably attach to each respective side via side attachment members.

Another embodiment of the invention may include the patient protection apparatus dimensioned and structured to removably engage the top surface of a patient platform. In this embodiment, the apparatus width may be smaller than a patient platform width and the apparatus length may be structured to extend from a position proximate a patient platform end to a position proximate a patient's upper torso. The apparatus may be structured to fit overtop of a patient's upper torso when the patient is laying on a patient platform.

In this embodiment, the front visor may include an arcuate bottom edge and a curved interface with the apparatus top. The first side and second side may each have a curved interface with the apparatus top, back, and front visor. The apparatus may further include a removably engaged tinted shield. The tinted shield may be removably engaged via at least one of top pegs fixedly attached to the apparatus top configured to accommodate corresponding holes in the tinted shield, hook and loop fasteners on the apparatus and the tinted shield, and oppositely charged magnets fixedly attached to the tinted shield and the apparatus.

This embodiment may include the back instrument aperture positioned in between and below two back arm apertures. The side instrument apertures may be positioned closer to the apparatus front than the side arm apertures and the filter interfaces may be positioned proximate a bottom front corner of the first side and second side respectively.

This embodiment may include securement members including at least one of a bottom gasket, hook and loop fasteners on the bottom surface of the apparatus structured to engage corresponding hook and loop fasteners on the top surface of the patient platform, and removably engaged adjustable straps removably secured to a device bottom lip at one end and an opposing end of the adjustable strap. Furthermore, the arm apertures and instrument apertures may each have a self-sealing medial passthrough surrounded by at least one of rubber and silicone structured to close the passthrough when not penetrated by a respective arm and instrument.

A top front enclosure may removably engage the apparatus top and extend to a patient torso edge. The top front enclosure may be structured to enclose a patient's upper torso within an apparatus hollow interior.

Another embodiment of the invention may include a patient protection apparatus including a first side and second side each with at least one of a side arm aperture, an instrument aperture, an air filter interface and a bottom securement member. It may have a back panel with a plurality of side arm apertures and at least one instrument aperture, a top, and a front visor.

The top may have a wider length at the front of the patient protection apparatus and a shorter length at the back. The first side and second side may taper at an angle from the front to the back and the apparatus may be structured to fit on top of a patient platform. The first side, second side, back, top and front visor may be structured to create a hollow interior that tapers from front to back.

Each respective side and back combination may be structured to accommodate a caretaker administering patient services utilizing one side arm aperture and one back arm aperture. The plurality of back arm apertures may be structured to accommodate at least one caretaker administering patient services utilizing two back arm apertures. Furthermore, the apparatus may be structured to accommodate a single caretaker utilizing a side arm aperture and back arm aperture simultaneously or two back arm apertures simultaneously. Likewise, the apparatus is structured to accommodate a plurality of caretakers utilizing at least one respective side arm aperture and one respective back arm aperture simultaneously.

Like the previous embodiment, the apparatus width may be structured to be smaller than a standard patient platform width. The apparatus length may be structured to extend from a position proximate a patient platform end to a position proximate a patient's upper torso. The apparatus may be structured to fit overtop of a patient's upper torso when the patient is laying on a patient platform.

Furthermore, the front visor may include an arcuate bottom edge and a curved interface with the apparatus top. The first side and second side may each have a curved interface with the apparatus top, back, and front visor. The arm apertures and instrument apertures may each have a self-sealing medial passthrough surrounded by at least one of rubber and silicone structured to close the passthrough when not penetrated by a respective arm and instrument.

In this embodiment, the apparatus interior may further include an adjustable light. The adjustable light may be one of fixedly attached to the apparatus interior top, removably attached to an apparatus interior side by way of holding device, and removably attached to the apparatus via magnet at the light base and opposingly charged magnet on the apparatus.

This embodiment may also have a filter interface with an interface plate including inside threading structured to accommodate a cap overtop and outside threading structured to accommodate a plug. A cap and plug may be structured to close the interface when not in use. The interface plate inside threading may be arranged to removably attach an adapter structured to accommodate a hose therein.

In some embodiments, the apparatus may further include an upper arm mount structured to removably attach a repositionable arm operable to position the apparatus onto and off of a patient platform. The repositionable arm may be structured to attach to a dental light arm. Additionally, the repositionable arm may further include at least one of a shield attachment member and tinted shield structured to adjustably screen a caretaker's eyes from reflected light. However, in some embodiments, the repositionable arm may be a self-supported freestanding structure.

DETAILED DESCRIPTION OF THE INVENTION

The present invention will now be described in detail with reference to the accompanying drawings. The embodiment descriptions are illustrative and not intended to be limiting in any way. Other embodiments of the invention will readily suggest themselves to persons with ordinary skill in the art after having the benefit of this disclosure. Accordingly, the following embodiments are set forth without any loss of generality and without imposing limitation upon the claimed invention.

Directional terms such as "above" "below" "upper" "lower" and other like terms are used for the convenience of the reader in reference to the drawings. Additionally, the description may contain terminology to convey position, orientation, and direction without departing from the principles of the present invention. Such positional language should be taken in context of the represented drawings.

Quantitative terms such as "generally" "substantially" "mostly" and other like terms are used to mean that the referred object, characteristic, or quality constitutes a majority of the referenced subject. Likewise, use of the terms such as first and second do not necessarily designate a limitation of quantity. Such terms may be used as a method of describing the presence of at least one of the referenced elements or may provide a means of differentiating orientation. The meaning of any term within this description is dependent upon the context within which it is used, and the meaning may be expressly modified.

Figure 1:
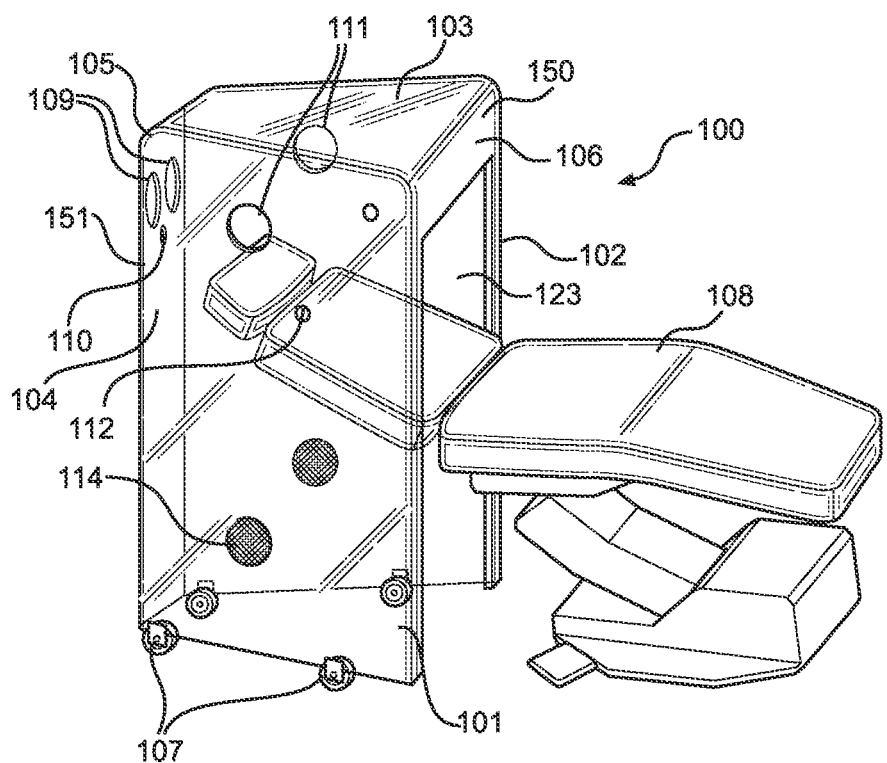
FIG. 1 is a right perspective view of a patient protection apparatus.

Referring now to FIG. 1, a patient protection apparatus 100, hereinafter referred to as the apparatus 100, will be described in more detail. The apparatus 100 may be a transparent or translucent housing 105 with at least one see-through first side 101, second side 102, back panel 104 and top surface 103. The front 150 of the apparatus 100 may generally be open exposing a hollow interior 123, with the exception of a front visor 106 extending downward from the top surface 103. The front visor 106 may connect the first side 101 to the second side 102 and in some embodiments may extend a distance of six inches distally from the top surface 103. However, in other embodiments the front visor 106 may extend more or less than six inches.

The top surface 103 may resemble a trapezoid with curved edges having a wider length at the front 150 of the apparatus 100 and a shorter length at the back 151 of the apparatus 100. Accordingly, the first side 101 and second side 102 may taper at an angle from the front 150 to the back 151 of the apparatus 100. This may allow for the hollow interior 123 to taper from front 150 to back 104. Furthermore, the entire housing 105 may be a single unit with rounded corners and edges. Additionally, the first side and second side may extend from a height proximate ground level to a height configured to accommodate a standard patient platform 108 with patient at either a horizontal or upwardly angled position.

In some embodiments the housing 105 may be a single extrusion made from clear rigid plastic material such as plexiglass. In other embodiments, the housing 105 may include a frame structured to accommodate either rigid plastic type material or flexible plastic sheets fitted around the frame. In any embodiment, the housing 105 may be structured so that the hollow interior 123 may accommodate at least a portion of a patient platform 108 therein. For purposes of this application, a patient platform 108 may include, but not be limited to an operating table, operating chair, dental table, dental chair, or the like.

Both the first side 101 and second side 102 of the apparatus 100 may include a side arm aperture 111, a side instrument aperture 112, a filter interface 114, and a pair of wheels 107. The side arm apertures 111 may be larger holes sized to accommodate a person's arm therethrough. The side instrument apertures 112 may be smaller holes sized to accommodate an instrument therethrough. Furthermore, it should be noted that the depicted drawings illustrate four arm apertures 109,111 and three instrument apertures 110, 112. However, it is contemplated to be within the scope of this application that the apparatus 100 may include more or less arm apertures 109, 111 and instrument apertures 110,112 depending on factors such as the size of the patient platform 108 as well as need and convenience of caretakers and attendants.

The side arm apertures 111 may be located near a top portion of each respective side 101,102 and may be located within the back half of each respective side 101, 102. Furthermore, the side instrument apertures 112 may be located below each respective side arm aperture 111. In some embodiments, side instrument apertures 112 may be six inches distal from the respective side arm aperture 111. However, in other embodiments a side instrument aperture 112 may be located more or less than six inches below the respective side arm aperture 111. Furthermore, in some embodiments the side arm apertures 111 may be located within an upper third of the apparatus 100. However, one skilled in the art will recognize that arm apertures 109,111 and instrument apertures 110,112 may be positioned elsewhere on the housing 105 according to factors such as the size of the patient platform 108 as well as need and convenience of caretakers and attendants.

Filter interfaces 114 may be structured to attach to a HEPA filter device in order to remove floating particles within the hollow interior 123 during patient procedures. One skilled in the art will appreciate that the filter interfaces 114 may be positioned at different locations throughout the housing 105. However, in the depicted embodiments the filter interfaces 114 are located within the bottom half of each respective side 101, 102 just above respective pairs of wheels 107.

Pairs of wheels 107 may be located at a bottom edge of the first side 101 and the second side 102. In some embodiments, the wheels 107 may be located on the interior of the apparatus 100 within the hollow interior 123. In other embodiments, the wheels 107 may be located on the exterior of each respective side 101,102. Although not shown, some embodiments may include a pair of wheels located on the bottom edge of the back panel 104 as well.

Figure 1A:
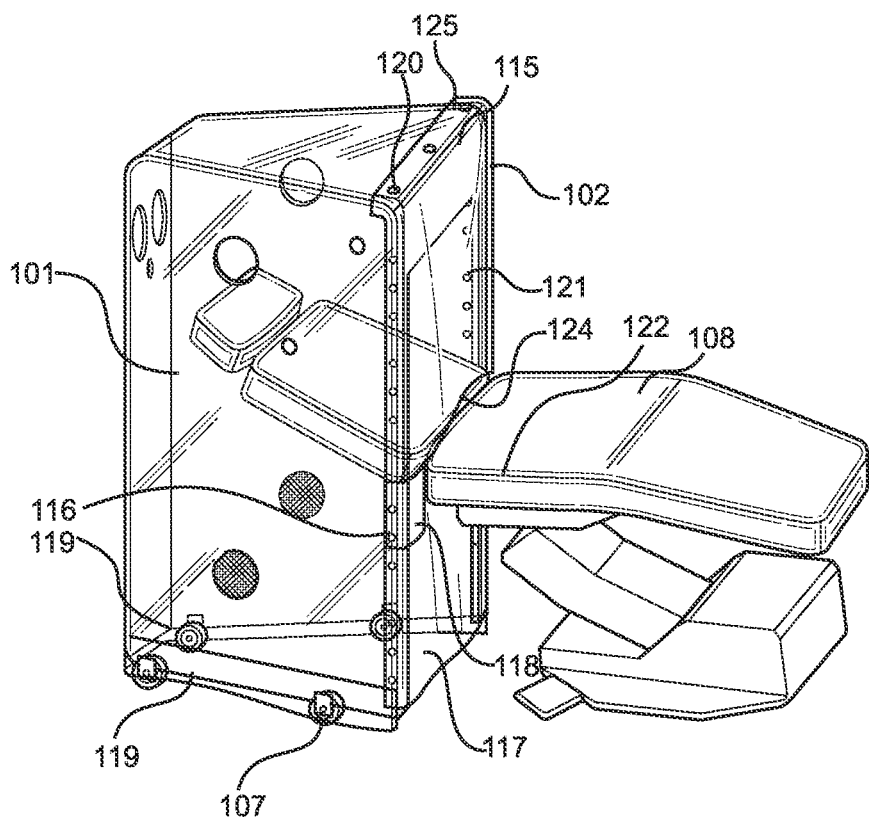
FIG. 1A is a right perspective view of the patient protection apparatus illustrated in FIG. 1 with attachment features according to an embodiment of the invention.

Referring to FIG. 1A, the apparatus 100 may include removable attachment features structured to enclose the hollow interior 123 and cover the wheels 107. Accordingly, the apparatus 100 may include a top front enclosure 115, a bottom front enclosure 117, and a wheel skirt 119. In some embodiments, attachment features may be made of fabric or plastic type material and may resemble drapes. However, attachment features may be clear plastic material designed to enclose the apparatus 100, while allowing visual contact with the hollow interior 123. These removable plastic type drapes may be structured to facilitate easy cleaning and replacement.

In this embodiment, the top front enclosure 115 may attach to the apparatus via a plurality of top attachment members 120. By way of non-limiting examples, top attachment members 120 may be snaps, hook and loop fasteners such as Velcro®, or twist lock fasteners that are fixedly attached to the top surface 103. The top attachment members 120 may have corresponding attachment members on the top front enclosure 115 so that the top front enclosure 115 may removably attach to the apparatus 100 at the top surface 103.

In this embodiment, the top front enclosure 115 may attach to the top surface 103 and extend over the front visor 106 at the visor overlap 125. It may further extend down the front 150 of the apparatus 100 and may overlay the first side 101 and second side 102 and removably attach thereto via side attachment members 121. By way of non-limiting examples, side attachment members 121 may be snaps, hook and loop fasteners such as Velcro®, or twist lock fasteners that are fixedly attached to the sides 101, 102 with counterparts located on the top front enclosure 115.

The top front enclosure 115 may extend from the first side 101 to the second side 102 at a first portion thereof. It may also extend downward from the top surface 103 to a horizontal section defined as the patient lap edge 124. The patient lap edge 124 may be at a length where the patient platform 108 crosses the threshold of the housing 105 into the hollow interior 123.

In this embodiment, the top front enclosure 115 may have an enclosure overhang 116 on either side of the patient lap edge 124. The enclosure overhang 116 may be side pieces structured to extend downward and around a patient platform 108. As shown in FIG. 1A, because patient platforms 108 may include contour edges 122, the enclosure overhang 116 may be structured to surround the patient platform 108 to facilitate a more complete enclosure of the hollow interior 123 when the patient platform 108 is located therein. The enclosure overhang 116 may removably attach to the first side 101 and second side 102 via the side attachment members 121. Furthermore, the enclosure overhang 116 may be structured to overlap a bottom front enclosure 117 at an enclosure overlap 118. In some embodiments the enclosure overlaps 118 may include attachment members to secure the top front enclosure 115 to the exterior facing surface of the bottom front enclosure 117. However, in other embodiments, the enclosure overlap 118 may hang freely overtop the bottom front enclosure 117.

The bottom front enclosure 117 may be made from the same material as the top front enclosure 115. It may also be removably attached to the first side 101 via side attachment members 121, extend across the front 150 of the apparatus 100, and removably attach to the second side 102 of the apparatus 100 via side attachment members 121. In some embodiments, the bottom front enclosure 117 may resemble a rectangle with side attachment members 121 on or proximate each width edge.

The wheel skirt 119 may removably attach to the first side 101, the back panel 104 and the second side 102 via attachment members. The wheel skirt 119 may be made of the same material as the bottom front enclosure 117 and the top front enclosure 115. In some embodiments, the wheel skirt 119 may extend from six inches above the bottom edges of the housing 105 to the bottom edges of the housing 105. However, in other embodiments the wheel skirt 119 may extend more or less than six inches. In some embodiments, the wheel skirt 119 may removably attach to the inside surfaces of the housing 105 and in other embodiments it may removably attach to the outside of the housing 105. In any embodiment, the wheel skirt 119 may be structured to attach to the housing 105 and removably cover the wheels 107. Furthermore, the wheel skirt 119 may be sized and positioned to removably attach to the housing 105 while covering the wheels 107 and lightly grazing the floor.

Figure 1B:
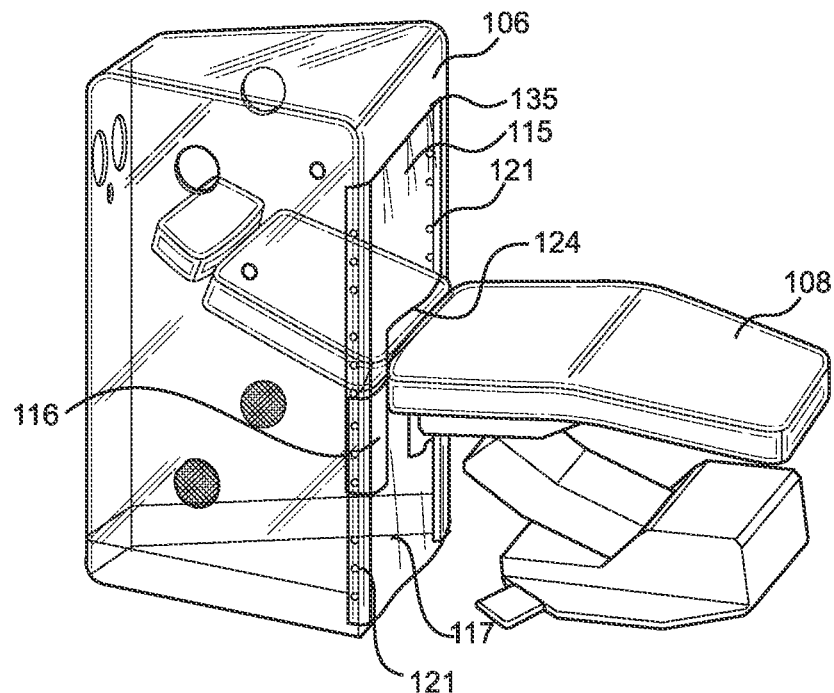
FIG. 1B is a right perspective view of the patient protection apparatus with attachment features according to another embodiment of the invention.
Figure 1C:
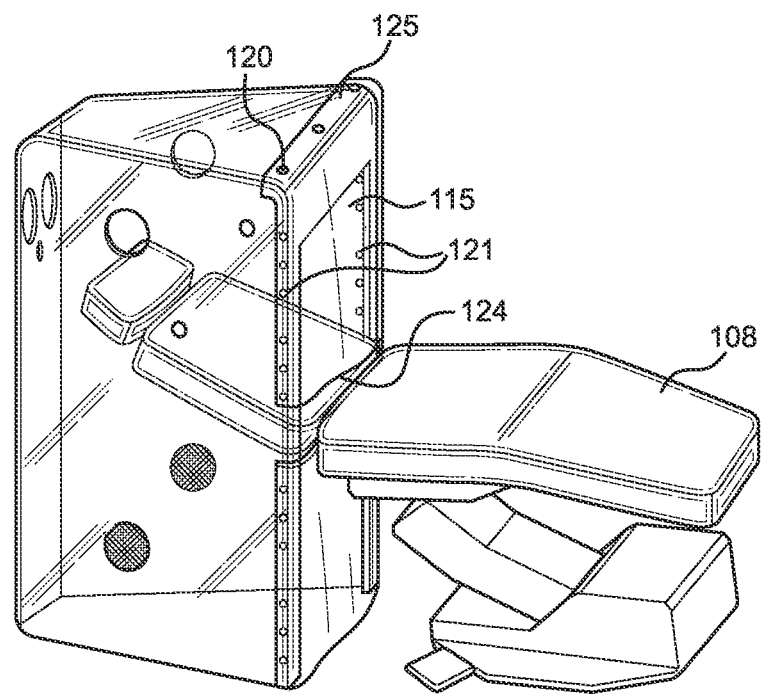
FIG. 1C is a right perspective view of the patient protection apparatus with attachment features according to another embodiment of the invention.
Figure 1D:
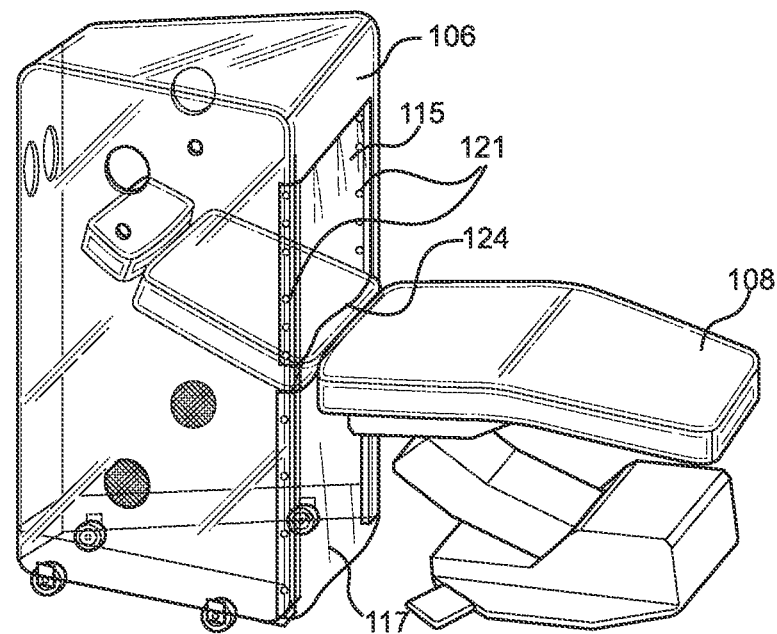
FIG. 1D is a right perspective view of the patient protection apparatus with attachment features according to another embodiment of the invention.

Referring now to FIGS. 1B, 1C, and 1D, other embodiments of the attachments to the apparatus 100 are shown. FIG. 1B demonstrates that in some embodiments the top front enclosure 115 may not include a visor overlap 125, but may instead include a top horizontal edge 135 that may abut or nominally overlap the front visor 106. FIG. 1C shows that the top front enclosure 115 may include a visor overlap 125 but may not include enclosure overhangs 116. In this embodiment, the top front enclosure 115 may terminate at the patient lap edge 124, which may extend across the entire length of the front 150 of the apparatus 100. FIG. 1D illustrates that in some embodiments the top front enclosure 115 may resemble the bottom front enclosure 117, which may terminate at the patient lap edge 124. It may include a top horizontal edge 135 that may abut or nominally overlap the front visor 106. In the embodiment depicted in FIG. 1D, the top front enclosure 115 may resemble a rectangle with side attachment members 121 on or proximate each width edge that may removably attach to each side 101,102 of the housing 100.

Figure 2:
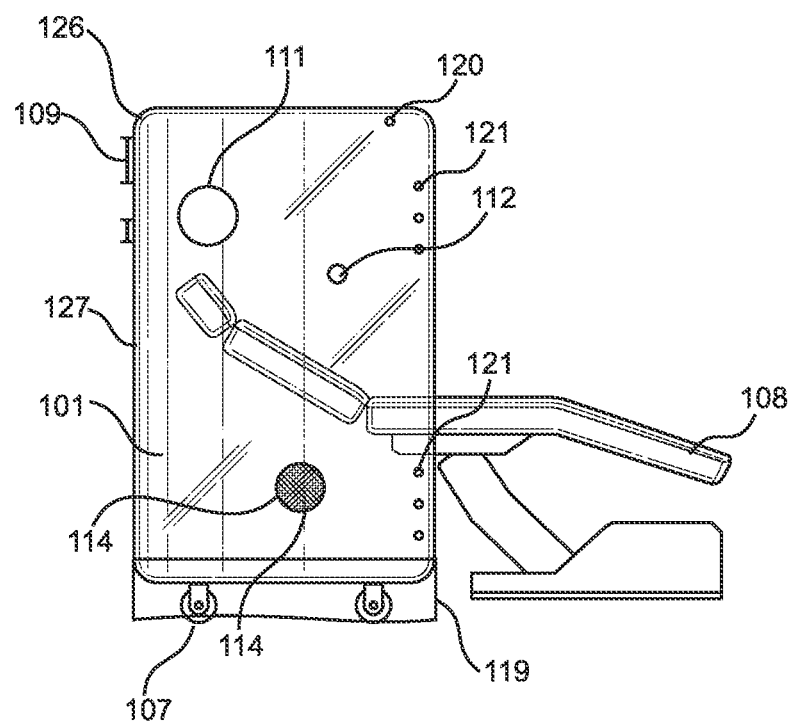
FIG. 2 is a right side view of the patient protection apparatus illustrated in FIG. 1.

FIG. 2 demonstrates a few of the key components in some embodiments of the apparatus 100 as taken from a planar view of the first side 101. In particular, this figure emphasizes the curved edges 122 of the housing 100 which may facilitate cleaning the apparatus 100 and prevent microbial and dirt buildup in corners and edges. Furthermore, this figure illustrates that in some embodiments the apparatus 100 may include a frame 127. The frame 127 may provide structural integrity for the housing 105 and as previously mentioned may be structured to accommodate either rigid plastic type material or flexible plastic sheets fitted thereon.

Figure 3:
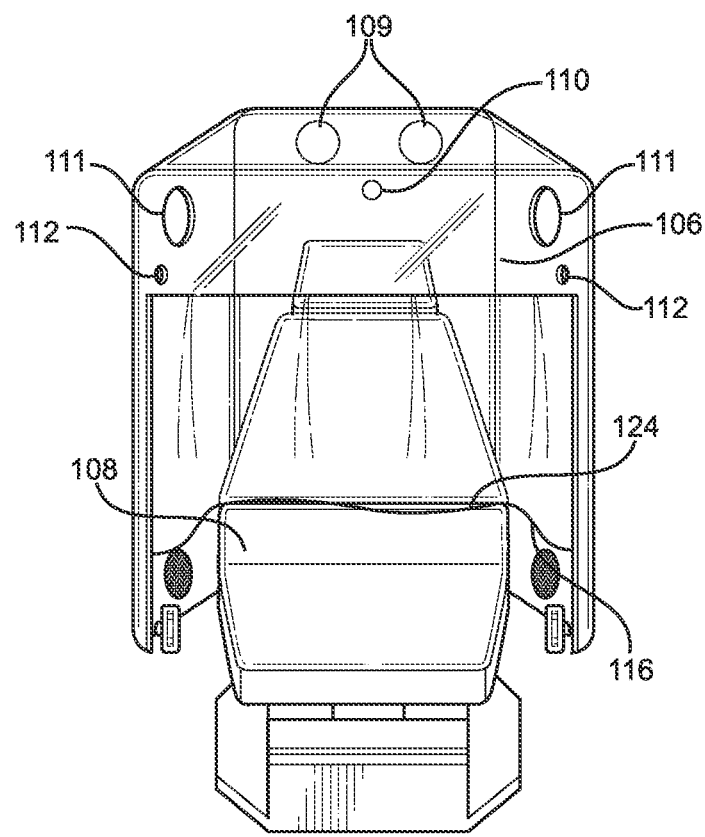
FIG. 3 is a front perspective view of the patient protection apparatus with attachment features according to an embodiment of the invention.
Figure 3A:
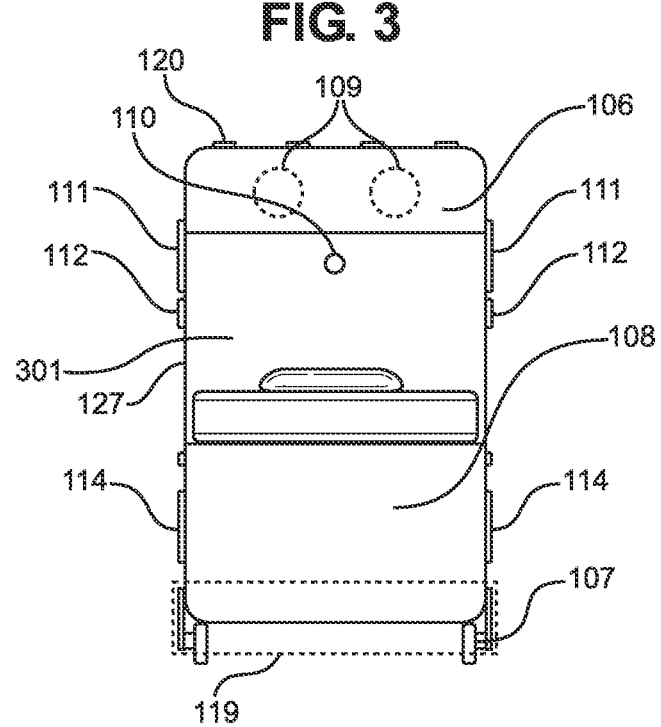
FIG. 3A is a front planar view of the patient protection apparatus according to an embodiment of the invention.
Figure 3B:
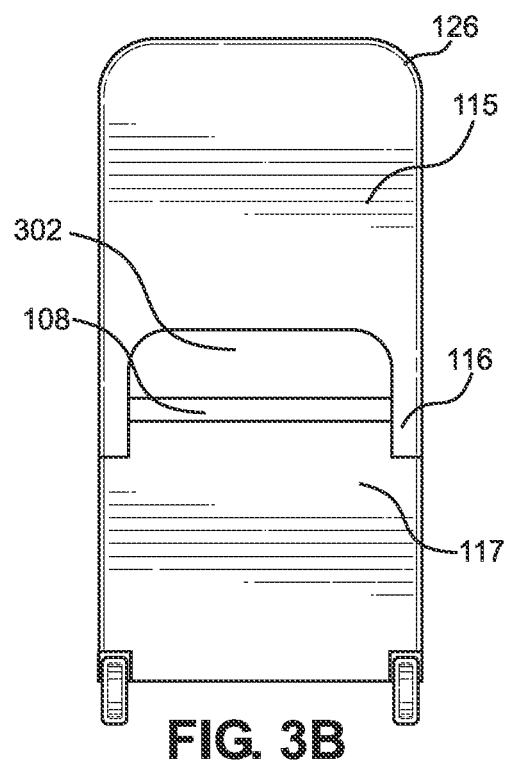
FIG. 3B is a front planar view of the patient protection apparatus with attachment features according to an embodiment of the invention.

FIGS. 3, 3A, and 3B demonstrate the apparatus 100 with attachments as viewed from the front 150. As shown by FIG. 3, the patient lap edge 124 may not always be straight across the front 150 of the apparatus. In some embodiments, the patient lap edge 124 may have enough slack to bunch at the patient platform 108 and fall down the sides thereof. Furthermore, the distance, placement, and apportionment of the back arm apertures 109, the side arm apertures 111, and the back instrument aperture 110 are more easily viewed from this angle. As demonstrated, the back arm apertures 109 may be proximate each other since the back panel 104 is a smaller width than the front 150. Furthermore, one back arm aperture 111 may be located proximate a respective side arm aperture 111. Additionally, the back instrument aperture 110 may be medially located below the back arm apertures 109. In some embodiments the back arm apertures 109 may be located within an upper third of the apparatus 100. However, a person skilled in the art will appreciate that the back arm apertures 109, the side arm apertures 111, the back instrument aperture 110 and the side instrument apertures 112 may be located anywhere on their respective sides and panel to facilitate their purpose.

FIG. 3B distinctly emphasizes the curved edges 126 of the front profile of the apparatus 100. Furthermore, a patient passthrough 302 is shown to demonstrate that the hollow interior 123 of the apparatus has been restricted to an opening sized only to accommodate a patient therethrough. The top front enclosure 115 with enclosure overhangs 116 in combination with the bottom front enclosure 117 may define a confined operating and procedural area within the hollow interior 123 of the housing 105.

Figure 4:
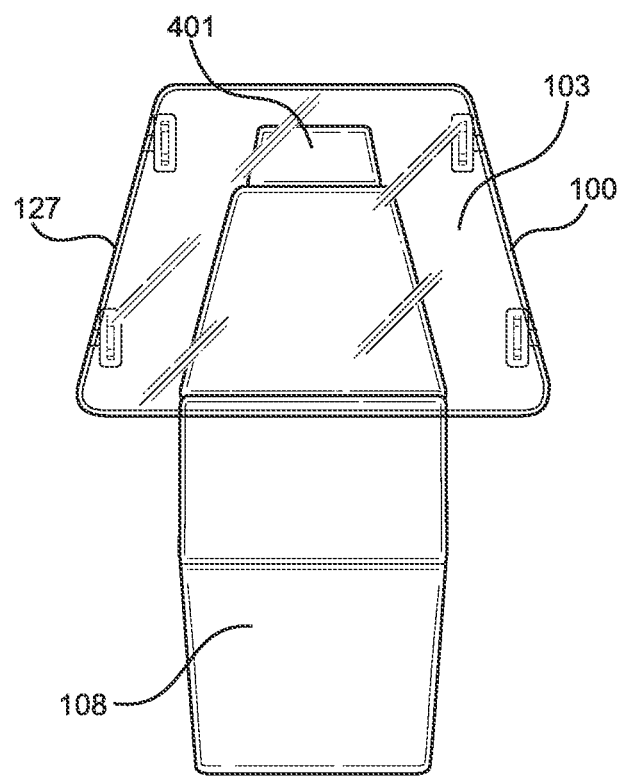
FIG. 4 is top planar view of the patient protection apparatus according to an embodiment of the invention.

FIG. 4 is a top-down view of the apparatus 100 emphasizing its overall shape being designed to conform to the shape of most patient platforms 108. Since many patient platforms 108 are wider at a midsection and narrower at a patient headrest 401, the apparatus 100 is tapered from front 150 to back 151 to accommodate. Furthermore, since many patient platforms 108 have contour edges 122 at the midsection, the pliant nature of the top front enclosure 115 allows it to effectively seal around the patient no matter the shape of the patient platform 108. Embodiments of the apparatus 100 include a housing 105 with rounded edges, rounded intersections and rounded corners to facilitate cleaning and to help prevent microbial and dirt buildup.

Figure 5:
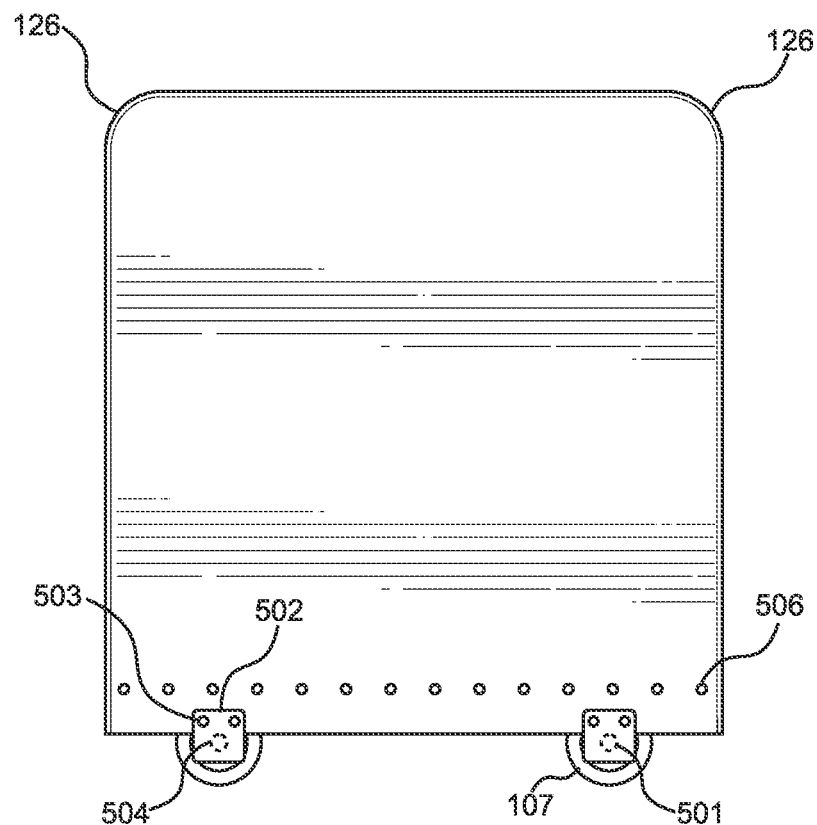
FIG. 5 is a side planar view of the patient protection apparatus according to an embodiment of the invention.

FIG. 5 is a side planar view of the apparatus 100 emphasizing curved edges 126, skirt attachment members 506, and the wheel attachment assembly 501. The skirt attachment members may align a bottom portion of the first side 101, the back panel 104 and the second side 102. In some embodiments, the skirt attachment members 506 may be snaps, hook and loop fasteners such as Velcro®, or twist lock fasteners that are fixedly attached to the sides 101, 102 and back panel 104 with counterparts located on the wheel skirt 119. The wheel skirt 119 may be removably attached around a periphery of the apparatus 100 via the skirt attachment members 506.

Figure 5A:
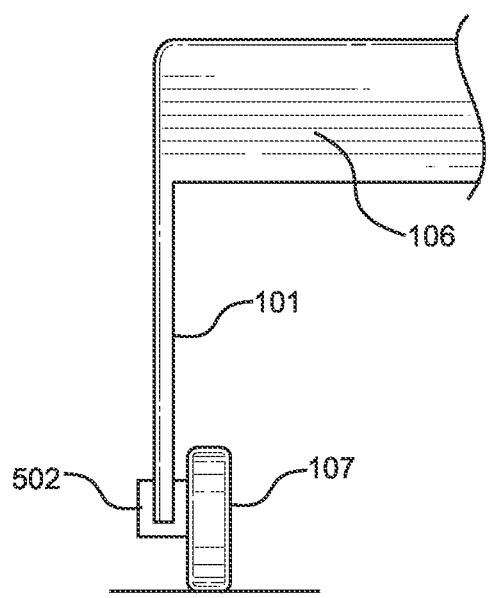
FIG. 5A is a front sectional view of the patient protection apparatus according to an embodiment of the invention.

Referring additionally to FIG. 5A, the wheel attachment assembly 501 may include an attachment bracket 502, bracket fasteners 503, and a wheel axis 504. The attachment bracket 502 may be a U-shaped brace structured to couple underneath a bottom edge of the first side 101 and second side 102. The attachment bracket 502 may attach to the first side 101 and second side 102 via the bracket fasteners 503. In some embodiments, the bracket fasteners 503 may be bolts or screws. In some embodiments, the bracket fasteners 503 may attach directly to the sides 101, 102 and in other embodiments the bracket fasteners 503 may pass through the sides 101, 102 and engage the attachment bracket 502 on the interior of the housing 105.

The wheel axis 504 may extend from an exterior facing surface of the wheel attachment assembly 501, pass through the attachment bracket 502, the sides 101, 102, and the wheel 107 to form a central rotation point for the wheel. In other embodiments the wheel axis 504 may extend from an interior facing portion of the attachment bracket 502 and engage a medial point of the wheel 107. As shown, the wheel 107 is located on the inside of the apparatus 100 within the hollow interior 123. However, other embodiments within the scope of this application include the wheel attachment assembly 501 reversed where the wheels 107 are on the outside of the apparatus 100. Likewise, some embodiments may include the wheel skirt 119 attaching to an exterior surface of the housing 105 and other embodiments include the wheel skirt 119 attaching to an interior surface of the housing 105 depending on the orientation of the wheels 107 and wheel attachment assembly 501.

Figure 6:
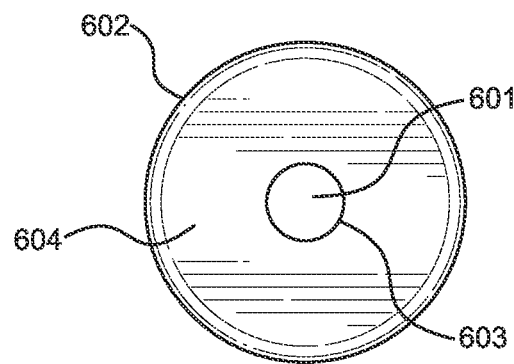
FIG. 6 is a planar view of an arm aperture of the patient protection apparatus according to an embodiment of the invention.

FIG. 6 is a planar view of a typical arm aperture 109, 111 according to one embodiment of the apparatus 100. The arm apertures 109, 111 may be holes in the sides 101, 102, and back panel 104 of the apparatus 100. These holes may consist of an outer perimeter 602 and an inner perimeter 603 surrounding a medial passthrough 601. Between the outer perimeter 602 and inner perimeter 603 may be sealing material 604 structured to circumscribe a caretaker's arm and make a seal therewith. This may prevent particulate material from escaping through the arm apertures 109,111 from the hollow interior 123. By way of non-limiting example, the sealing material 604 may be made of silicone, rubber, plastic, or a combination thereof.

Similarly, instrument apertures 110, 112 may be holes in the sides 101, 102, and back panel 104 of the apparatus 100. These holes may consist of an outer perimeter 602 and an inner perimeter 603 surrounding a medial passthrough 601. Between the outer perimeter 602 and inner perimeter 603 may be sealing material 604 structured to circumscribe a caretaker's instrument to make a seal therewith. This may prevent particulate matter from escaping through the instrument apertures 110, 112 from the hollow interior 123. By way of non-limiting example, the sealing material 604 may be made of silicone, rubber, plastic, or a combination thereof.

Furthermore, both arm apertures 109,111 and instrument apertures 110, 112 may include aperture covers (not shown) for use with unused apertures. This may prevent particulate matter from escaping through holes in the apparatus 100 that are not sealed by instruments or a caretaker's arm. In some embodiments these aperture covers may resemble the top front enclosure 115, bottom front enclosure 117 and the wheel skirt 119 in material, composition, and attachment members 120, 121.

In other embodiments, the aperture covers may be plugs sized to fit into the medial passthrough 601. These plugs may be made of the same sealing material 604 used between the outer perimeter 602 and inner perimeter 603.

Figure 7:
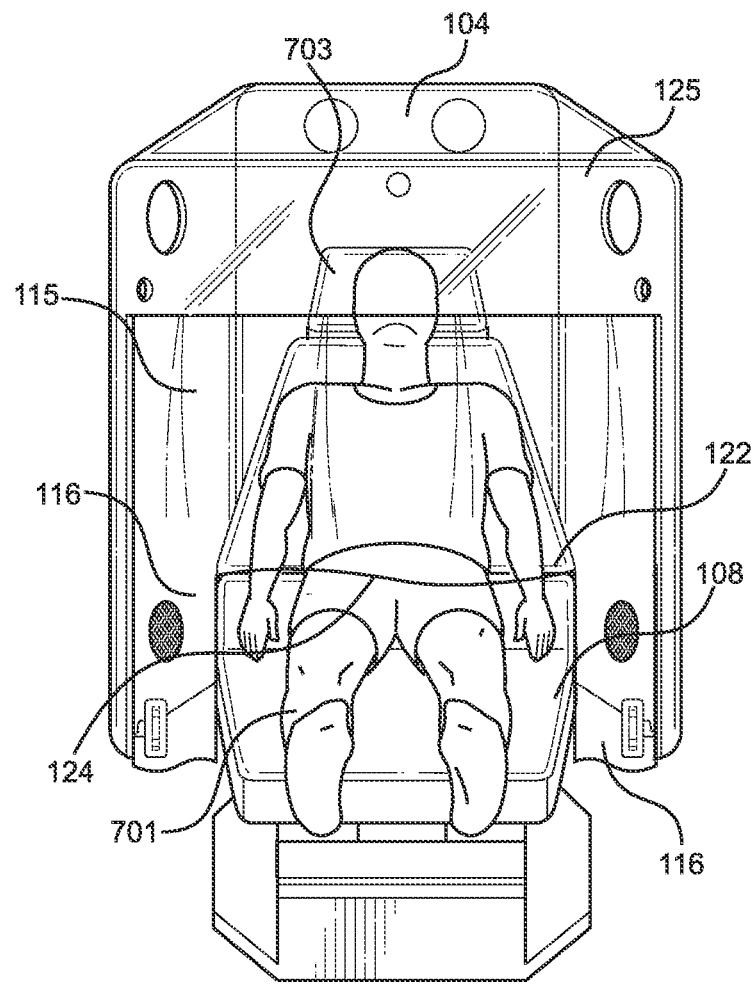
FIG. 7 is a front perspective environmental view of the patient protection apparatus according to an embodiment of the invention.
Figure 7A:
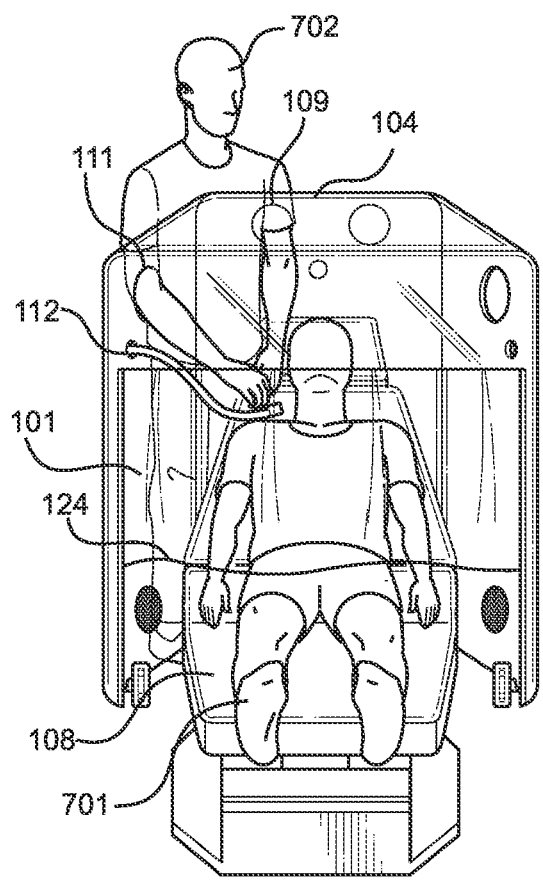
FIG. 7A is a front perspective environmental view of the patient protection apparatus according to an embodiment of the invention.
Figure 7B:
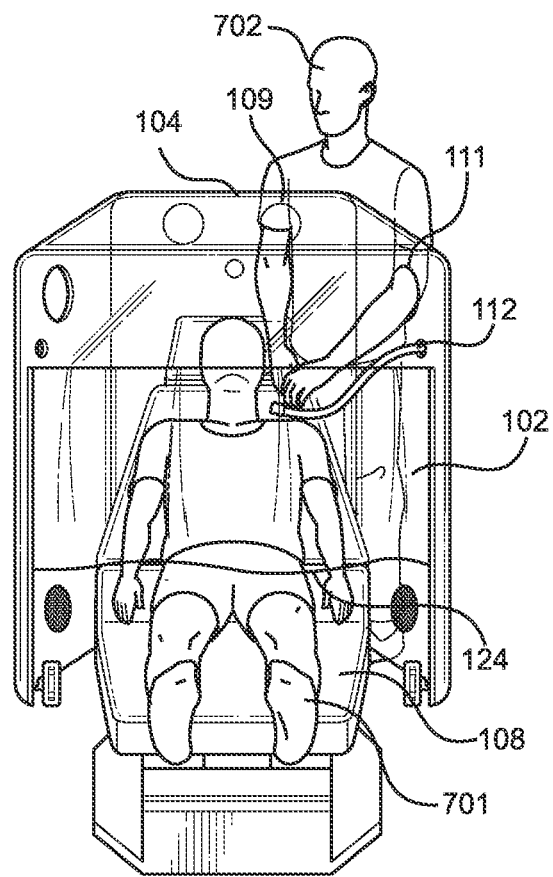
FIG. 7B is a front perspective environmental view of the patient protection apparatus according to an embodiment of the invention.
Figure 7C:
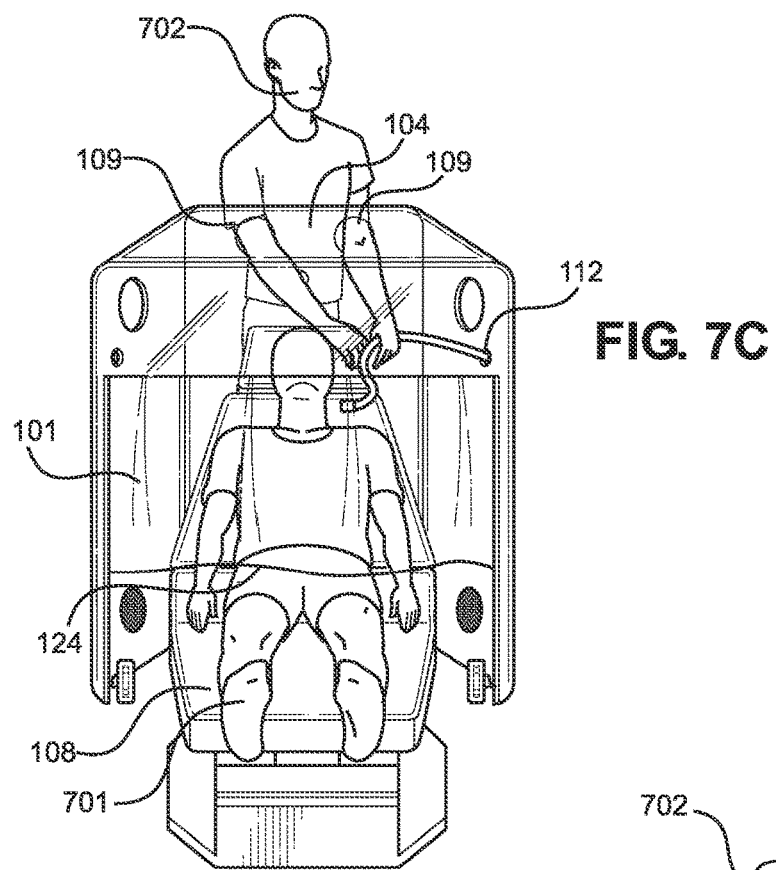
FIG. 7C is a front perspective environmental view of the patient protection apparatus according to an embodiment of the invention.
Figure 7D:
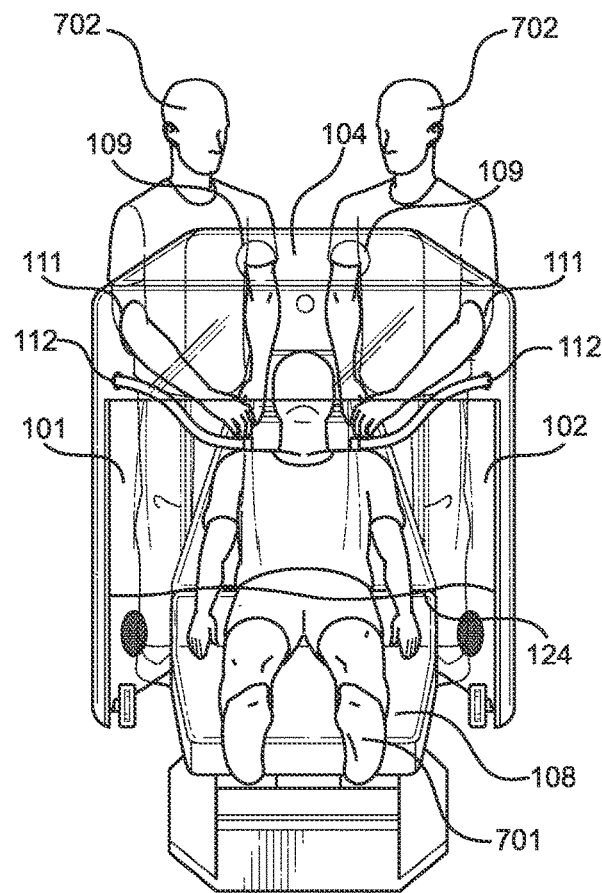
FIG. 7D is a front perspective environmental view of the patient protection apparatus according to an embodiment of the invention.

FIGS. 7 through 7D demonstrate the functional features of the apparatus 100. Although not specifically shown, the apparatus 100 is portable and may be wheeled to patient platforms 108 when needed. When preparing for its use, the attachment features are removed exposing the entire front 150 with front visor 106 and hollow interior 123. The front 150 of the apparatus 100 may be wheeled overtop a patient platform 108 until the head 703 of the patient platform 108 is proximate the back panel 104. At this point, a substantial portion of the patient platform 108 may be within the hollow interior 123. A patient 701 may be initially laying on the patient platform 108 before it is wheeled, or in some instances the patient 701 may lay on the patient platform 108 after the apparatus 100 has been put into place. Since most patient platforms 108 are either mechanical or hydraulic and able to be lifted into position, the section of the patient platform 108 supporting a patient's 701 head may be raised to a height sufficient to be accessed by the arm apertures 109, 111 and instrument apertures 110,112.

Now the attachment features of the apparatus may be put into place. The top front enclosure 115 may be attached to the top surface 103 and/or the sides 101, 102 where appropriate and the patient lap edge 124 may fall on the patient's 701 lap. Embodiments with enclosure overhangs 116 may have them extend downward around the patient platform 108 and patient 701.

FIG. 7 shows the top front enclosure 115 resembling a transparent curtain whereby undulated edges of the patient lap edge 124 rest on the patient's 701 lap. Contour edges 122 of the patient platform 108 are covered by the top front enclosure 115. The bottom front enclosure 117 may already have been attached, or if not, may be attached at this point. Likewise, the wheel skirt 119 may already have been attached, or if not, may be attached at this point.

FIGS. 7A through 7D demonstrate how a caretaker 702 may use the apparatus 100. In FIG. 7A a caretaker is using a side arm aperture 111 on the first side 101 in conjunction with a back arm aperture 109 on the back panel 104. In this particular instance, an instrument is being used on the side instrument aperture 112. However, one skilled in the art will recognize that the back instrument aperture 110 or opposing side instrument aperture may be used while the caretaker 702 is in this position. The patient 701 is enclosed within the apparatus 100 and the caretaker 702 may safely perform procedures while containing errant particulate matter within the hollow interior 123.

FIG. 7B illustrates a caretaker 702 utilizing the other back arm aperture 109 in conjunction with the side arm aperture 111 on the second side 102. In this instance, an instrument is being used on the side instrument aperture 112. However, one skilled in the art will recognize that the back instrument aperture 110 or opposing side instrument aperture 112 may be used while the caretaker 702 is in this position. With this apparatus, an individual caretaker 702 may utilize the positioning in either 7A or 7B depending on preference, arm dominance, and convenience.

FIG. 7C illustrates that a caretaker 702 may utilize both back arm apertures 109 to access the patient. In this particular instance, an instrument is being used on the side instrument aperture 112. However, one skilled in the art will recognize that the back instrument aperture 110 or opposing side instrument aperture may be used while the caretaker 702 is in this position.

FIG. 7D demonstrates the versatility of the apparatus 100 by showing two caretakers 702 simultaneously accessing the patient 701 whereby one caretaker 702 is utilizing a back arm aperture 109 and a side arm aperture 111 on the first side 101 and another caretaker 702 is utilizing a back arm aperture 109 and side arm aperture 111 on the second side 102. Furthermore, both side instrument apertures 112 are being utilized. However, one skilled in the art will recognize that the back instrument aperture 110 may also be used instead of or in addition to the side instrument apertures 112 depending on need and convenience.

Figure 8:
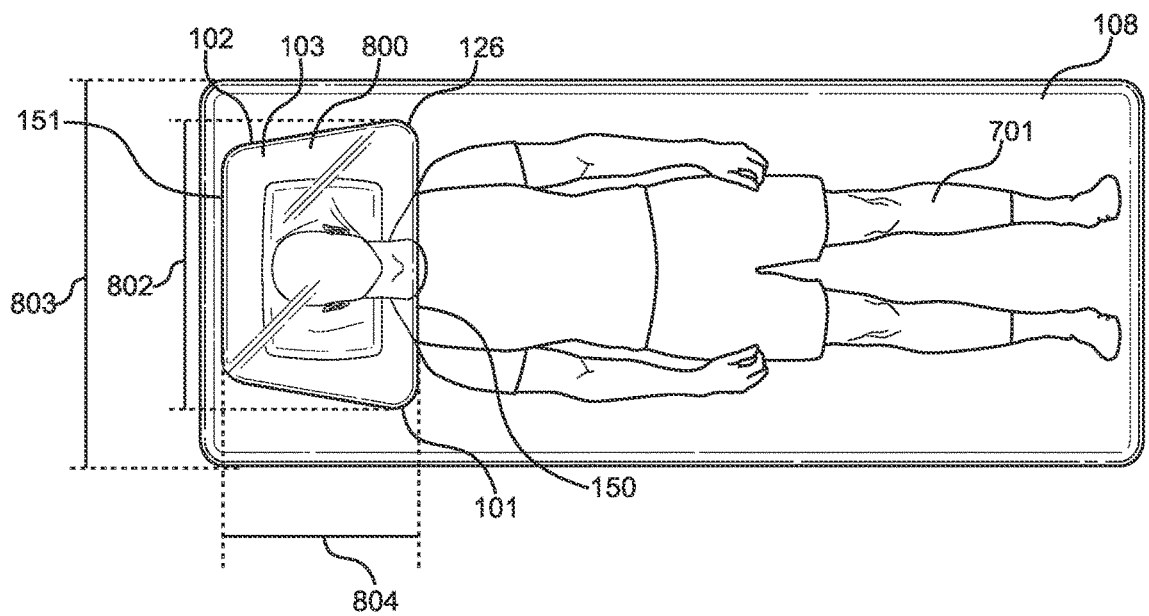
FIG. 8 is a top environmental view of another embodiment of the patient protection apparatus.

FIG. 8 shows a top view of another embodiment of the apparatus 800. In this embodiment the apparatus 800 may structurally resemble the previously described embodiment without wheels 107. Instead, the apparatus 800 may have an apparatus width 802 that is dimensioned to fit comfortably on top of a patient platform 108 between a platform width 803. An apparatus length 804 may be structured to extend from just past a patient's 701 head to proximate where a patient's 701 neck meets their shoulder. In other words, the apparatus width 802 may be structured to be smaller than a patient platform width 803. The apparatus length 804 may be structured to extend from a position proximate a patient platform end to a position proximate a patient's upper torso. Additionally, the apparatus 800 may be structured to fit overtop of a patient's upper torso when the patient 701 is laying on a patient platform 108.

Like the previous embodiment, the top surface 103 may resemble a trapezoid with curved edges having a wider length at the front 150 of the apparatus 800 and a less wide length at the back 151 of the apparatus 800. Accordingly, the first side 101 and second side 102 may taper at an angle from the front 150 to the back 151 of the apparatus 800. Furthermore, the entire apparatus 800 may be a single unit with rounded corners and curved edges 126.

Figure 9:
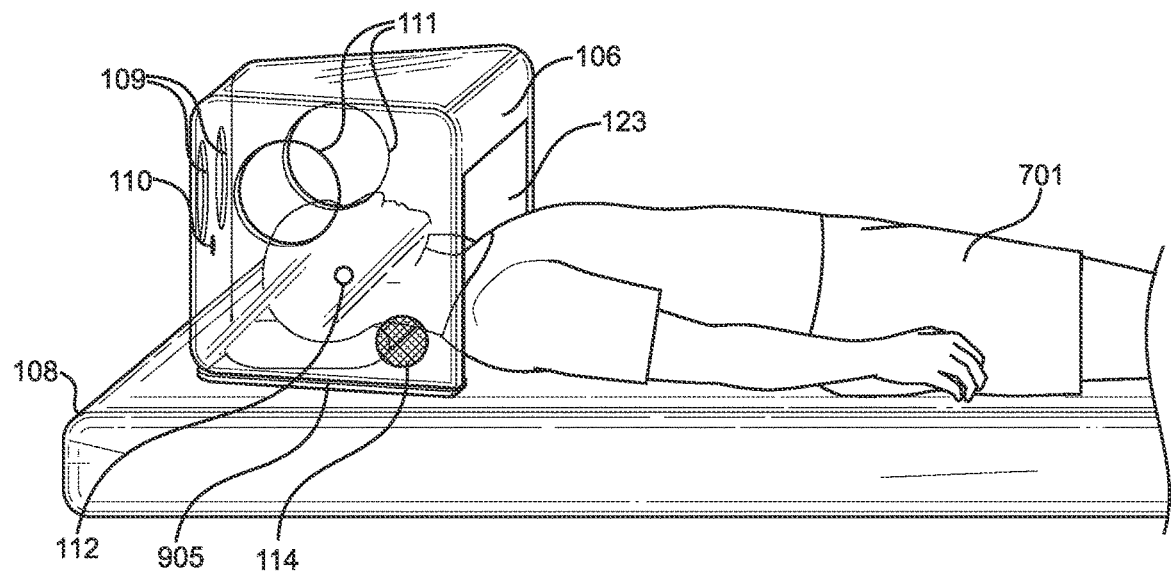
FIG. 9 is a right perspective environmental view of the patient protection apparatus illustrated in FIG. 8.

FIG. 9 is a right perspective view of the apparatus 800 and demonstrates that, like the previous embodiment, the apparatus 800 may include a front visor 106, side arm apertures 111, side instrument apertures 112, back arm apertures 109, back instrument apertures 110, and filter interfaces 114. Furthermore, the apparatus 800 may include a hollow interior 123 to accommodate a patient 701 therein that may taper from front 150 to back 151.

Like the previous embodiment, it should be noted that depicted drawings of this embodiment 800 illustrate four arm apertures 109,111 and three instrument apertures 110, 112. However, it is contemplated to be within the scope of this application that the apparatus 800 may include more or less arm apertures 109, 111 and instrument apertures 110,112 depending on factors such as the size of the patient platform 108 as well as need and convenience of caretakers 702 and attendants.

Both structurally and functionally, the components of this apparatus 800 embodiment resemble the previous apparatus 100 embodiment. Positioning and orientation of the components may differ slightly according to size of the apparatus 800 as well as need and convenience. However, because this apparatus 800 embodiment may removably rest on top of a patient platform 108, it may include a bottom securement member 905, which in some embodiments may be a bottom gasket, on the bottom edges of the apparatus 800. In some embodiments, the bottom securement member 905 may frictionally engage the patient platform 108 to facilitate a secure and steady placement of the apparatus 800 and help prevent it from prolapsing on the patient platform 108. In some embodiments, as will be shown hereinafter, the bottom securement member 905 may be at least one of a bottom gasket, hook and loop fasteners on the bottom surface of the apparatus 800 structured to engage corresponding hook and loop fasteners on the top surface of the patient platform 108, and removably engaged adjustable straps removably secured to the apparatus at one end and an opposing end of the adjustable strap.

In this embodiment, the back instrument aperture 110 may be positioned in between and below the two back arm apertures 109 and the side instrument apertures 112 may be positioned closer to the front 150 than the side arm apertures 111. In other embodiments, this positioning may be reversed whereby the side arm apertures 111 are closer to the front than the side instrument apertures 112. Additionally, the filter interfaces 114 may be positioned proximate a bottom front corner of the first side and second side 101, 102 respectively.

Figure 10:
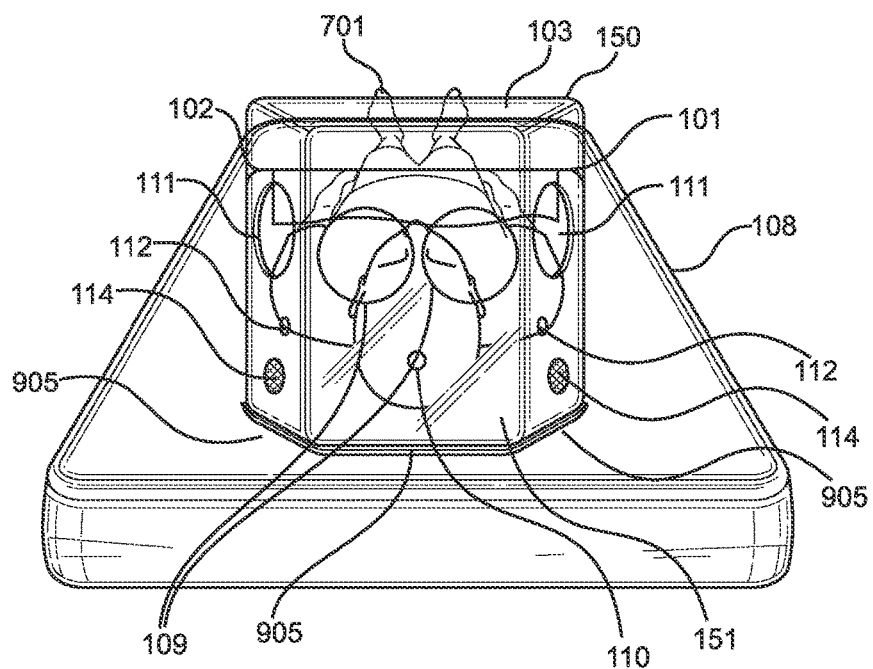
FIG. 10 is a rear perspective environmental view of the patient protection apparatus illustrated in FIG. 8.

FIG. 10 is a rear perspective view of the patient protection apparatus 800. This view emphasizes the angle of the apparatus 800 from back 151 to front 150. Like the previous apparatus 100 embodiment, this apparatus 800 embodiment may have a wider length at the front 150 that is greater than the back 151. Furthermore, this view clearly depicts all three bottom securement members 905 securing the apparatus 800 on top of the patient platform 108.

Figure 11A:
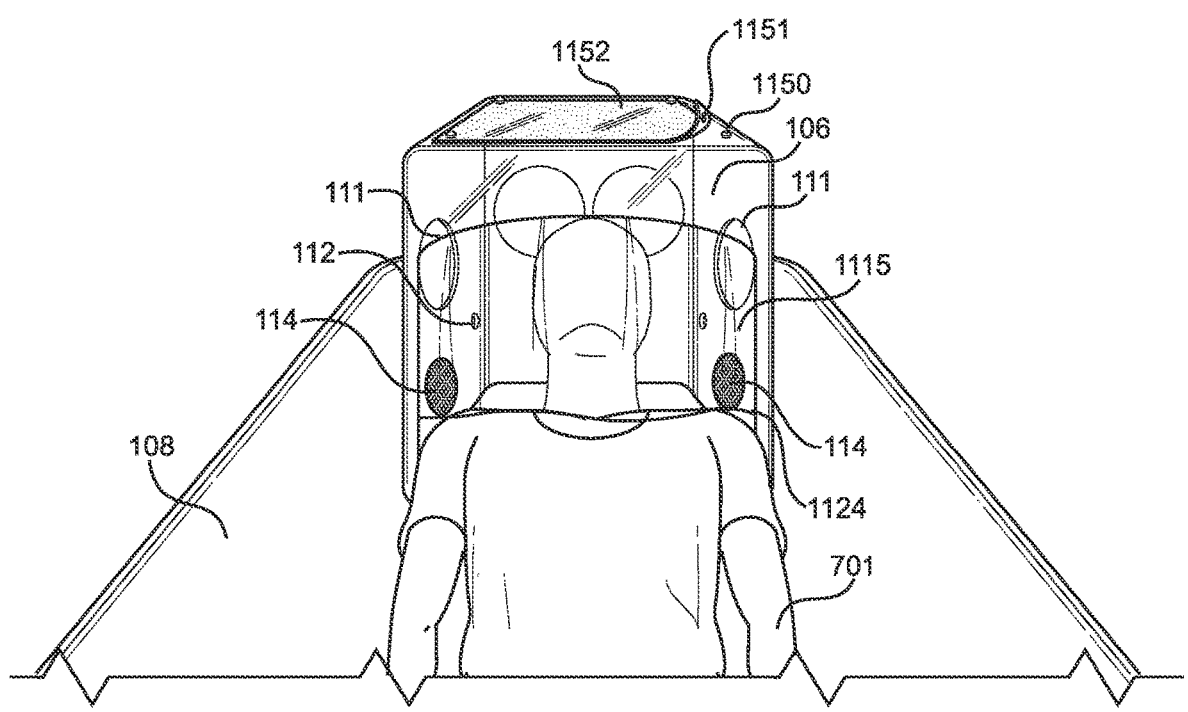
FIG. 11A is a front perspective environmental view of the patient protection apparatus illustrated in FIG. 8.

FIG. 11A is a front perspective view of the patient protection apparatus 800. This view also emphasizes the tapered structure of the apparatus 800 from front 150 to back 151. Like the previous apparatus 100 embodiment, this apparatus 800 embodiment may include a top front enclosure 1115 and a patient edge 1124.

Figure 11B:
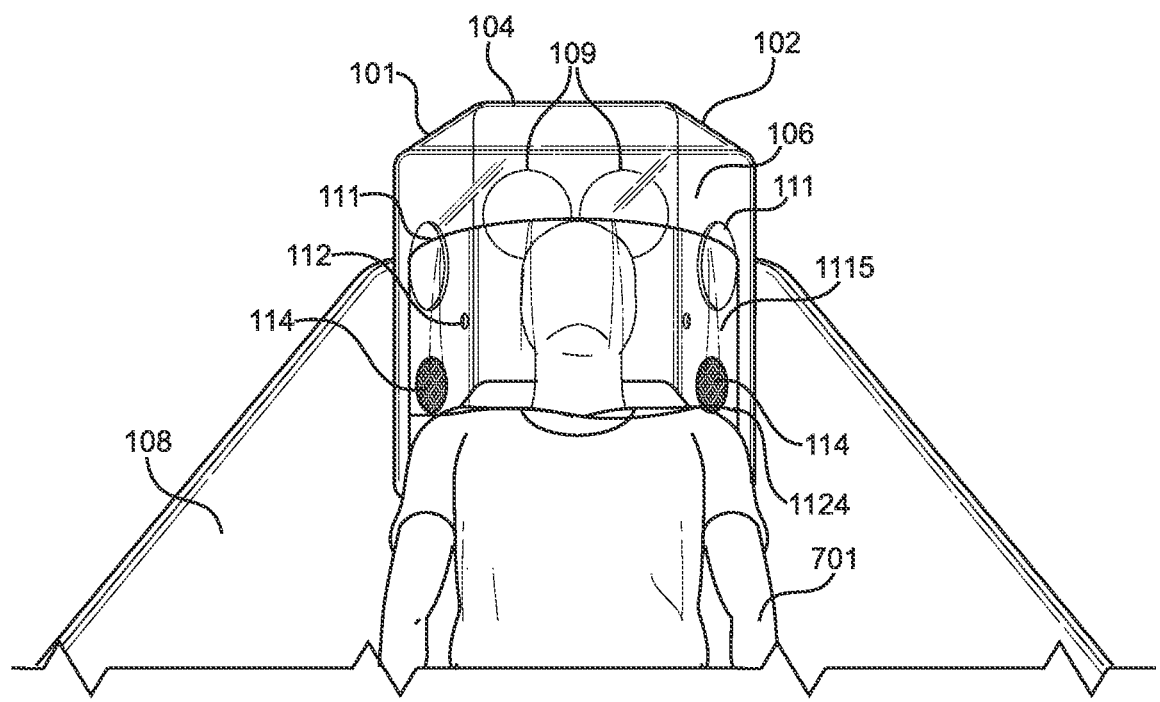
FIG. 11B is a front perspective environmental view of the patient protection apparatus illustrated in FIG. 8 according to an embodiment of the invention.

The removable attachment features and embodiments of the apparatus 800 top front enclosure 1115 may be similar to the previous apparatus 100. Meaning, the top front enclosure 1115 may have embodiments where it removably attaches to the top surface 103 and sides 101, 102 and includes a visor overlap 125. In some embodiments the top front enclosure 1115 may not include a visor overlap 125, but may instead include a top horizontal edge 135 that may abut or nominally overlap the front visor 106. As FIGS. 11A and 11B illustrate, the front visor 106 may include an arcuate bottom edge and a curved interface with the apparatus top 103. Furthermore, the first and second sides 101, 102 may each have a curved interface with the apparatus top 103, back 104, and front visor 106.

In some embodiments the top front enclosure 1115 may include a visor overlap 125 but may not include enclosure overhangs 116. In this embodiment, the top front enclosure 1115 may terminate at the patient edge 1124, which may extend across the entire length of the front 150 of the apparatus 800. Since the apparatus 800 terminates at the patient platform 108, this apparatus 800 embodiment may not include as extensive of an enclosure overhang 116, if any. In any embodiment with a top front enclosure 1115, the top front enclosure 1115 may be structured to removably engage the apparatus top 103, extend to a patient 701 torso edge and enclose a patient's 701 upper torso within an apparatus 800 hollow interior 123.

Use and functionality of the apparatus 800 may be similar to those depicted in FIGS. 7A through 7D. In particular, the apparatus 800 may be utilized by one or more caretakers 702 positioned at either the first side 101, second side 102, back panel 104, or a combination thereof. Furthermore, the caretakers 701 may utilize one or more of the side arm apertures 111, back arm apertures 109, side instrument apertures 112 or back instrument apertures 110 depending on need and convenience. Like the previous apparatus 100 embodiment, this apparatus 800 embodiment may be structured to accommodate a single caretaker 701 utilizing a side arm aperture 111 and back arm aperture 109 simultaneously or two back arm apertures 109 simultaneously. The apparatus 800 is also structured to accommodate a plurality of caretakers 701 utilizing at least one respective side arm aperture 111 and one respective back arm aperture 109 simultaneously.

FIG. 11B is a front perspective environmental view of the patient protection apparatus according to an embodiment of the invention illustrating that the apparatus 800 may include a removably engaged tinted shield 1152. The tinted shield 1152 may be removably engaged to the apparatus 100, 800 via at least one of top pegs 1150 fixedly attached to the apparatus top surface 103 structured to accommodate corresponding holes in the tinted shield 1152. However, in other embodiments the tinted shield 1152 may be attached to the apparatus 100, 800 via hook and loop fasteners on the apparatus 100, 800 and the tinted shield 1152. Still, in other embodiment the tinted shield 1152 may be attached to the apparatus 100, 800 via oppositely charged magnets fixedly attached to the tinted shield 1152 and the apparatus 100, 800. In some embodiments, the tinted shield 1508 may be made of a rigid, translucent or transparent material which may include plastic, polycarbonate and the like. It may include a thickness of ⅛ of an inch and in some embodiments may be colored orange, blue, green, or the like. However, one skilled in the art will appreciate that the thickness may be more or less and the color may vary depending on need, preference and circumstance.

Figure 12A:
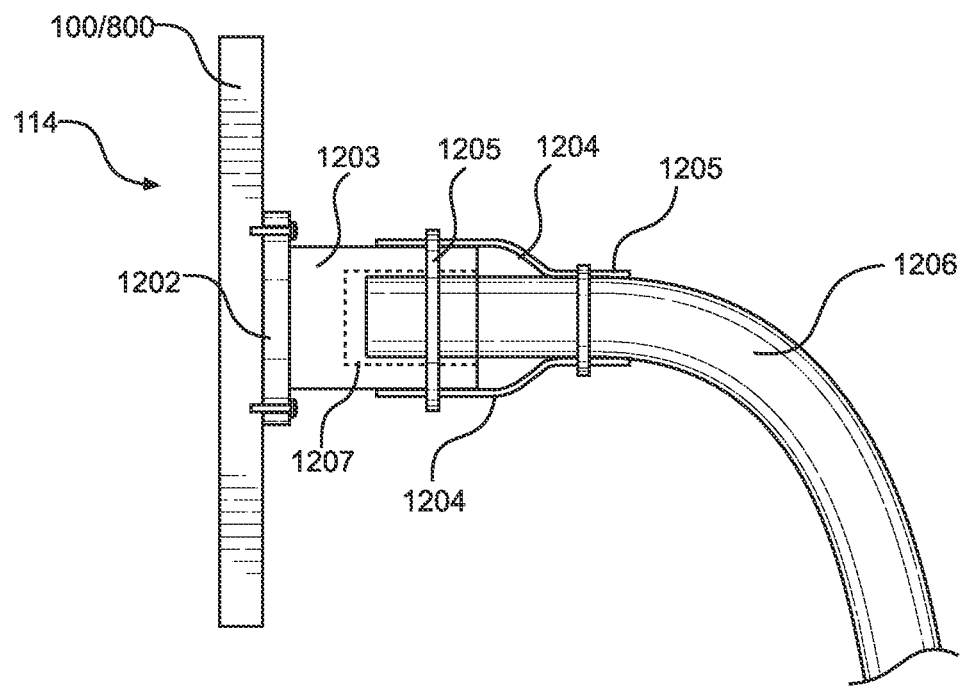
FIG. 12A is a side cross section of the patient protection apparatus filter interface assembly according to an embodiment of the invention.
Figure 12B:
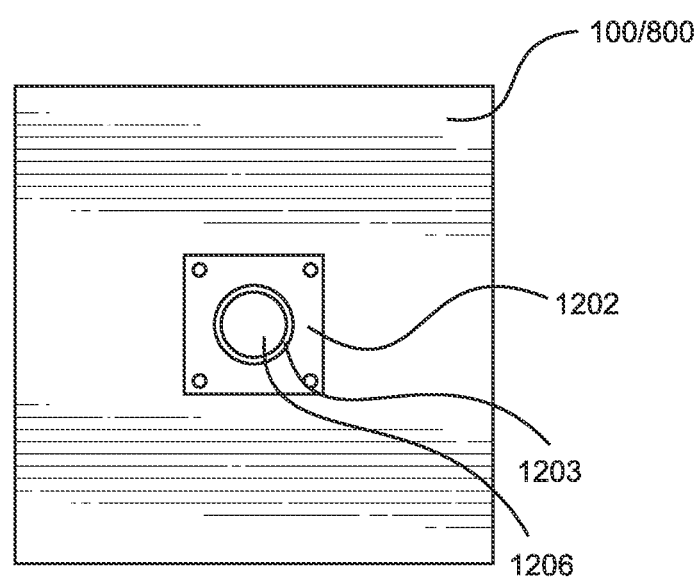
FIG. 12B is front view of the patient protection apparatus filter interface assembly according to an embodiment of the invention.

FIGS. 12A and 12B take a closer look at the filter interface 114 on the patient protection apparatus 100, 800. Both the first and second sides 101, 102 may include an interface plate 1202 with threading on one or both of the inside and outside of the interface plate 1202. The threading on the outside of the interface plate 1202 may be used as a means to removably attach a cap to the filter interface 114 to close it off when not being used. The threading on the inside may be used as a means to removably attach a plug to the filter interface 114 to close it off when not being used. In some embodiments, the threading on the interior of the interface plate 1202 may be used to removably attach an adapter member 1203. In other embodiments, the adapter member 1203 may be a friction fit with the interface plate 1202.

The adapter member 1203 may be an elongate extension with one side structured to removably engage the apparatus 100, 800 and an opposing side structured to receive a hose 1206 such as an HVAC hose or the like. The end of the adapter member 1203 distal to the apparatus 100, 800 may be structured to accommodate several differently sized hoses 1206. By way of non-limiting example, the adapter member 1203 may include a wider opening on the outside and a narrower opening more toward the inside. In this embodiment, a wider hose 1206 may connect via friction fit to the outer and wider opening or alternatively a narrower hose 1206 may bypass that fitting and connect via friction fit to an inner narrower opening. However, in some embodiments the adapter member 1203 may be interchangeable with other adapter members with differently sized distal openings to accommodate differently sized hoses 1206.

In some embodiments, the filter interface 114 may be an assembly including an interface plate 1202, an adapter member 1203, a supportive sleeve 1204, and securing straps 1205. The supportive sleeve 1204 may fit around the adapter member 1203 and a hose 1206. The securing straps 1205 may then wrap around an end of the supportive sleeve 1204 that fits overtop of the adapter member 1203 and may wrap around an end of the supportive sleeve that fits overtop of the hose 1206. The securing straps 1205 may secure to themselves by means of hook and loop fastener, snap, buckle, or the like. The combination of the adapter member 1203, the supportive sleeve 1204 and the securing straps 1205 may allow for a supported and flush filter interface 114 connection and may help prevent kinks in the hose 1206.

Figure 13A:
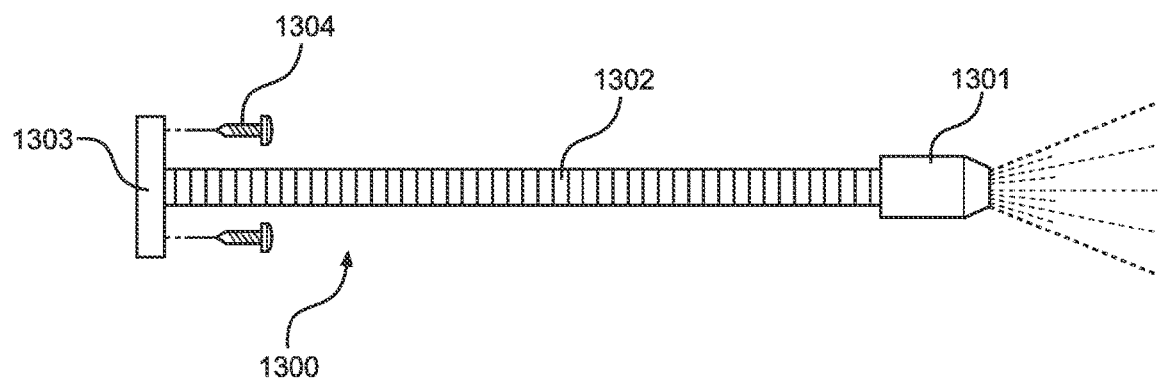
FIG. 13A is a side view of the patient protection apparatus light assembly according to an embodiment of the invention.

FIG. 13A illustrates a light assembly 1300 that may be included on the interior of the patient protective apparatus 800. In some embodiments, the light assembly 1300 may include a light 1301 with an adjustable arm 1302, a mounting member 1303 and mounting fasteners 1304. The light assembly 1300 may be structured to fit inside the apparatus 100, 800 and the adjustable arm 1302 may be directed to position the light 1301 in accordance with a caretaker's need, preference, and circumstance.

Figure 13B:
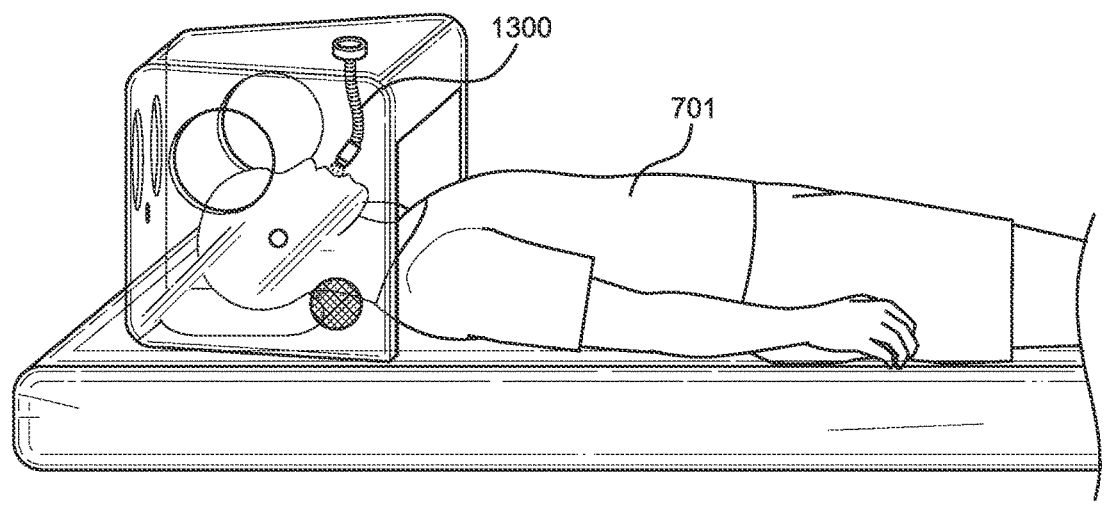
FIG. 13B is a side perspective environmental view of the patient protection apparatus light assembly according to an embodiment of the invention.

FIG. 13B illustrates that in some embodiments, the light assembly 1300 may be fixedly attached to an interior top of the apparatus 100, 800 whereby the light 1301 is directly attached thereto via the mounting fasteners 1304. However, in some embodiments the light assembly 1300 may be removably attach to the apparatus 800 via magnet at the light base and opposingly charged magnet on the apparatus 800.

Figure 13C:
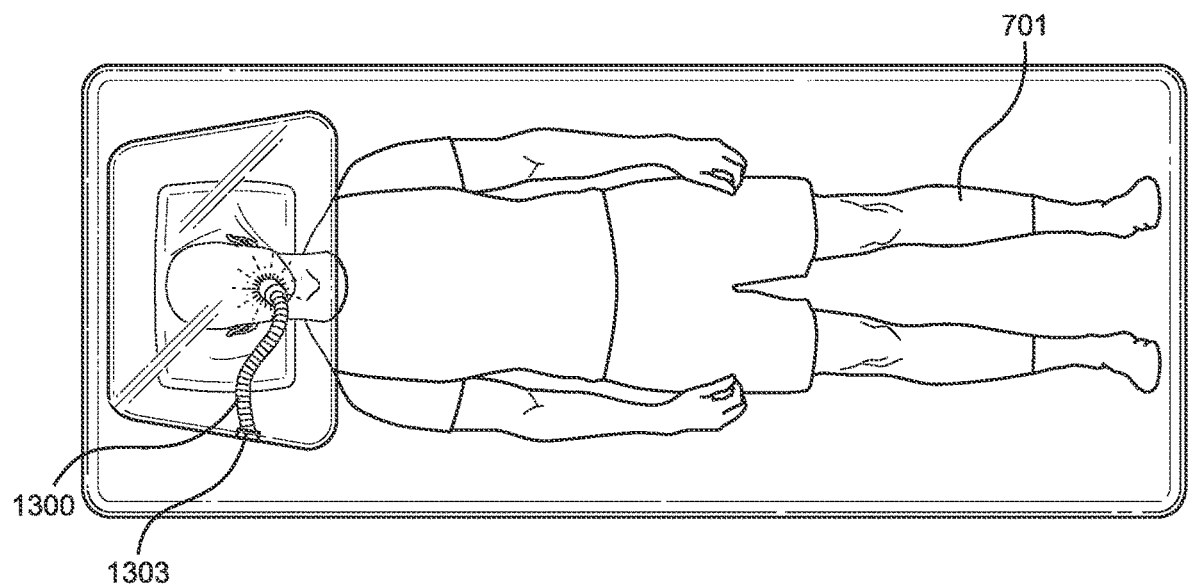
FIG. 13C is a top perspective environmental view of the patient protection apparatus light assembly according to an embodiment of the invention.
Figure 13D:
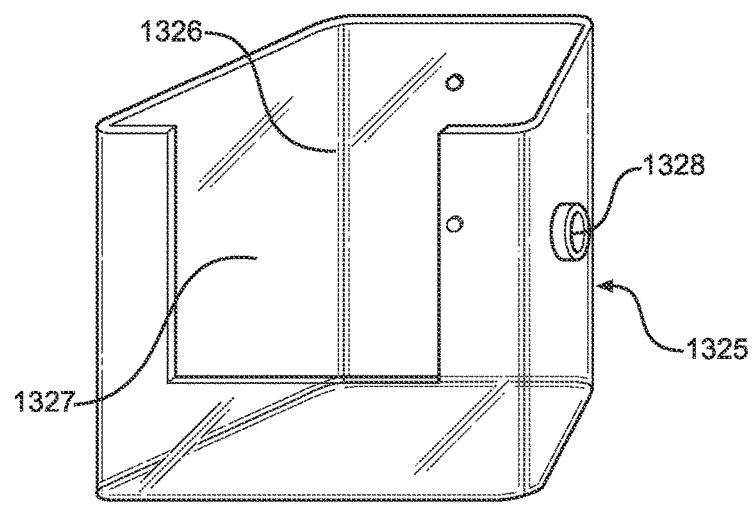
FIG. 13D is a front perspective view of a patient protection apparatus light assembly base holder member according to an embodiment of the invention.

FIGS. 13C and 13D illustrate that in some embodiments the light assembly 1300 may be removably attached to a side of the apparatus 100, 800 utilizing a base holder 1325 structured to accommodate the mounting member 1303 therein. The base holder 1325 may include a holding void 1326 structured to hold the mounting member 1303. A support notch 1327 may allow for the adjustable arm 1301 to protrude through a front portion of the base holder 1325 while adding support. In some embodiments, the mounting member 1303 may be fixedly attached to a back portion of the base holder 1325 via mounting fasteners 1304 and in other embodiments the mounting member 1303 may simply rest within the base holder 1325 being leveraged by the holding void 1326, the support notch 1327 and the walls of the base holder 1325. In some embodiments, the base holder 1325 may include a cord outlet 1328 allowing for an electrical cord to be easily fitted therethrough.

Figure 14A:
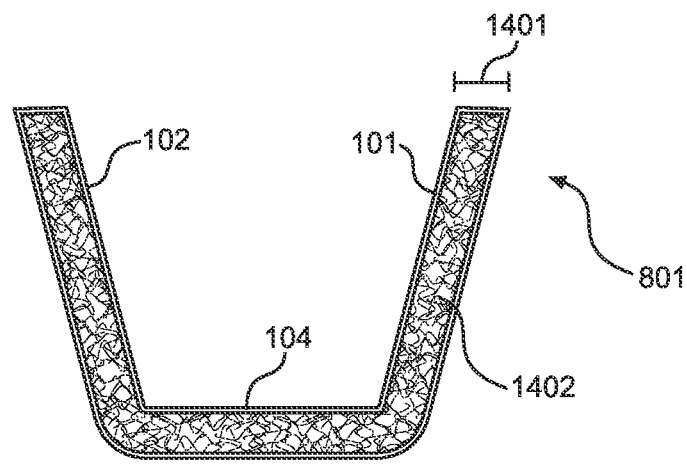
FIG. 14A is a bottom view of a patient protection apparatus according to an embodiment of the invention.

FIG. 14A illustrates an embodiment of the apparatus 800 that may include a bottom lip 1401 extending distally from the bottom of the first and second sides 101, 102 as well as the back 104. In some embodiments, the bottom lip 1401 may include hook and loop fasteners 1402 structured to removably engage the top surface of a patient platform 108 that is also equipped with hook and loop fasteners.

Figure 14B:
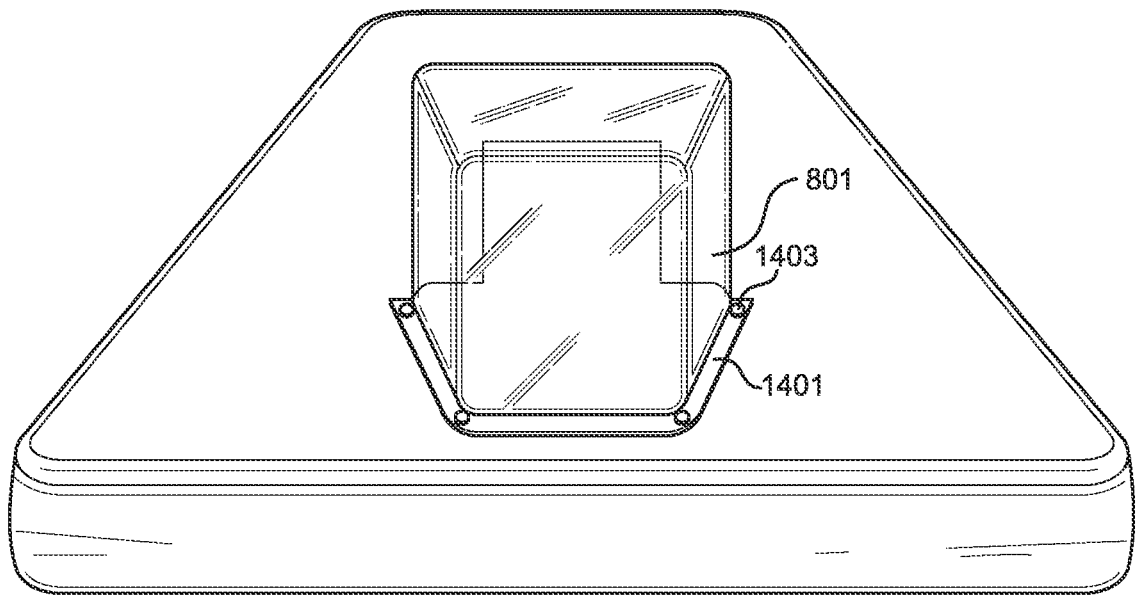
FIG. 14B is a back perspective environmental view of the patient protection apparatus according to an embodiment of the invention.

FIG. 14B shows an embodiment whereby the bottom lip 1401 may be engaged with the top surface of a patient platform 108 with corner fasteners 1403. The corner fasteners 1403 may be segments of hook and loop fasteners or may be snaps.

Figure 14C:
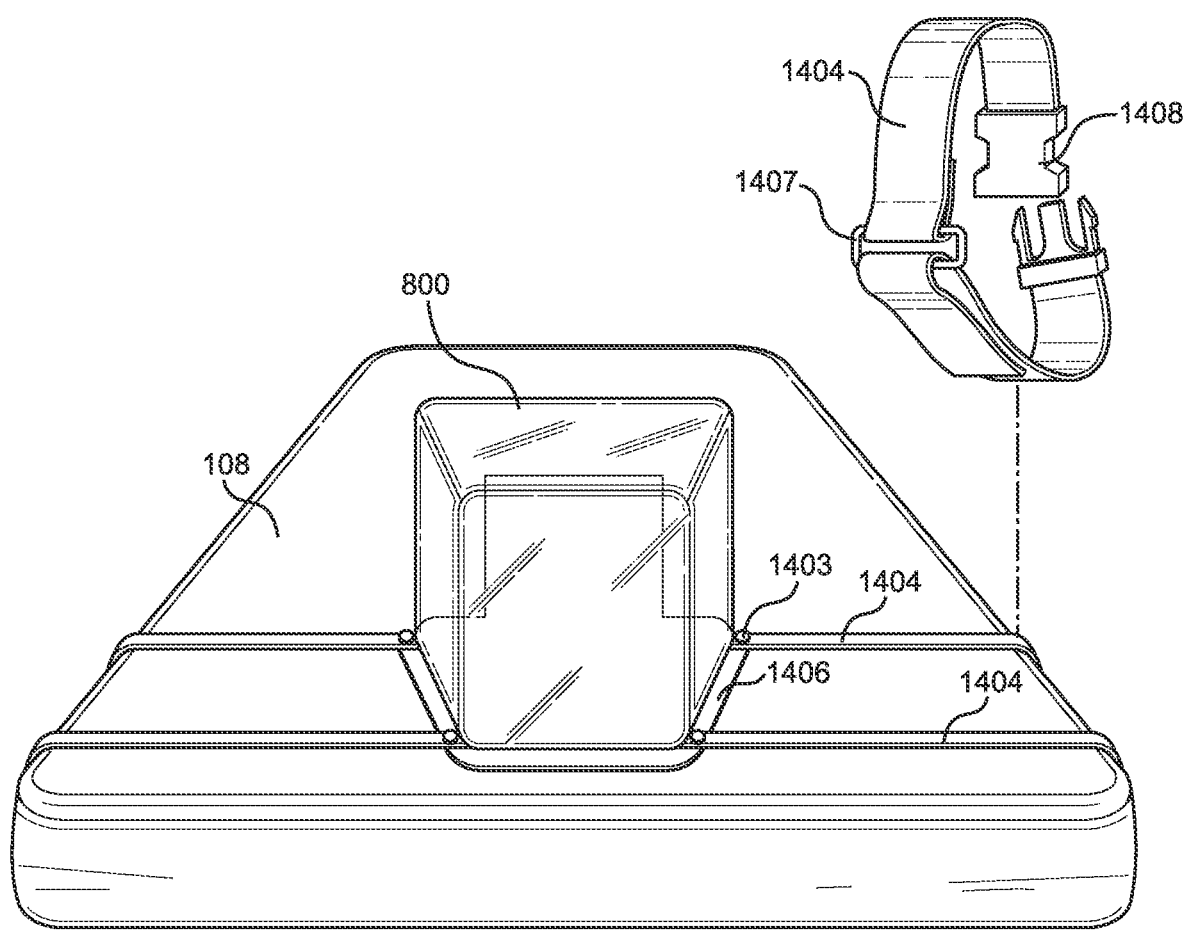
FIG. 14C is a back perspective environmental view of the patient protection apparatus according to an embodiment of the invention.

FIG. 14C illustrates an embodiment whereby adjustable straps 1404 may be removably attached to corner fasteners 1403 on the top surface 1406 of the bottom lip 1401 at one end of each respective adjustable strap 1404. The adjustable straps 1404 may be structured to wrap around a patient platform 108 and attach to themselves at opposing ends via buckle 1408 in order to better secure the apparatus 800 on the patient platform 108. Furthermore, the adjustable straps 1404 may include a cinch 1407 structured to tighten or loosen the adjustable straps 1404 accordingly.

Figure 15A:
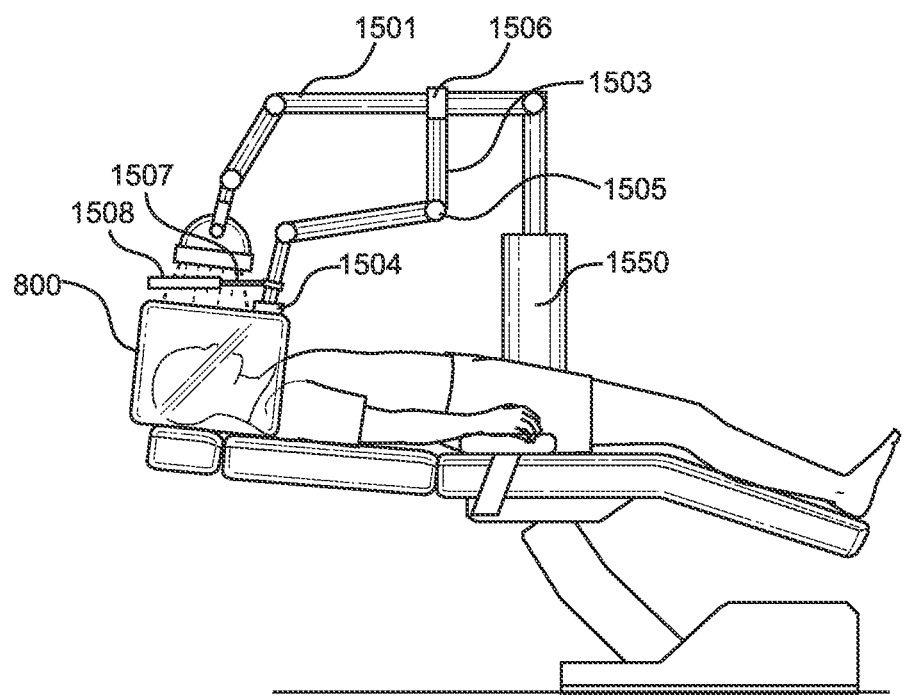
FIG. 15A is a side perspective environmental view of the patient protection apparatus according to an embodiment of the invention.

FIG. 15A illustrates an embodiment of the apparatus 800 whereby it is held in place by a repositionable arm 1503. In this embodiment, the repositionable arm 1503 may attach to a light fixture 1550 found in the art. By way of non-limiting example, this light fixture 1550 may be a light commonly used with dental chairs. In this embodiment, the repositionable arm 1503 may be attached to the light fixture 1550 at one end and may be attached to the apparatus 800 via arm mount 1504 at another end. In some embodiments, the repositionable arm 1503 may be attached to the dental chair light fixture 1550 via swivel that may enable the apparatus 800 to swing toward and away from a patient platform 108. Furthermore, the repositionable arm 1503 may include a plurality of hinge joints 1505 structured to orient the repositionable arm 1503 and as a result orient the apparatus 800 in a desired position. In some embodiments, the repositionable arm 1503 may include a shield attachment member 1507 and tinted shield 1508 configured to adjustably screen a caretaker's eyes from reflected light. In some embodiments, the tinted shield 1508 may be made of a rigid, translucent or transparent material and may be made of plastic, polycarbonate or the like. It may include a thickness of ⅛ of an inch and in some embodiments may be colored orange, blue, green, or the like. However, one skilled in the art will appreciate that the thickness may be more or less and the color may vary depending on need, preference and circumstance.

Figure 15B:
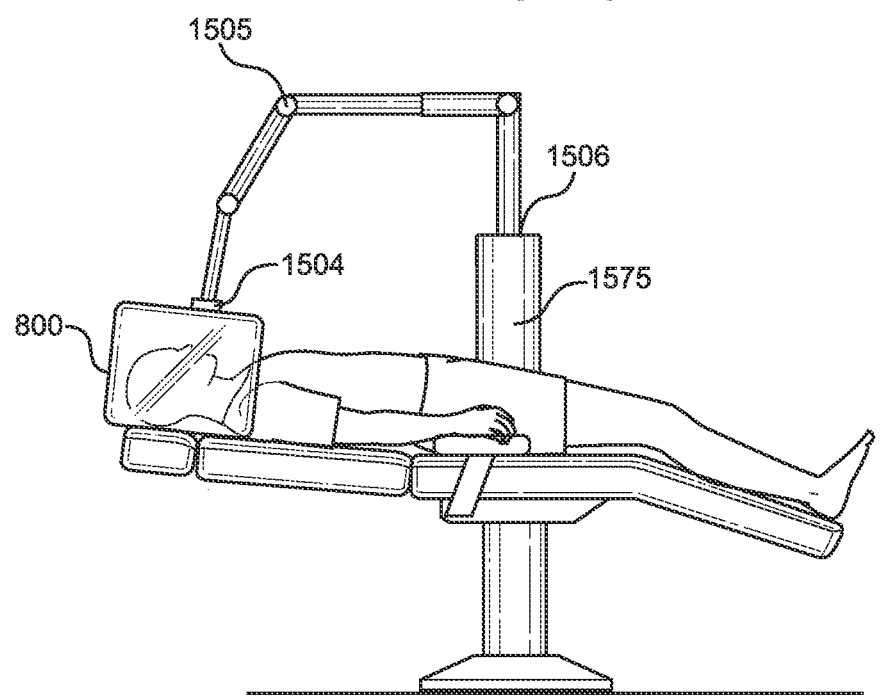
FIG. 15B is a side perspective environmental view of the patient protection apparatus according to an embodiment of the invention.

FIG. 15B illustrates an embodiment whereby the repositionable arm 1503 is attached to its own self-supported freestanding structure 1575. In this embodiment, the entire self-supported freestanding structure 1575 may be moved toward and away from the patient platform 108 as needed. However, in some embodiments there may be a swivel 1506 positioned at a vertical base 1576 of the self-supported freestanding structure 1575. Furthermore, the repositionable arm 1503 may additionally be repositioned via plurality of hinge joints 1505 as well.

That which is claimed is:

1. A patient protection apparatus comprising
a first side and second side each comprising at least one of a side arm aperture, an instrument aperture, an air filter interface and a pair of wheels,
a back comprising a plurality of back arm apertures and at least one back instrument aperture,
a top, and
a front visor,
wherein the top has a wider length at a front of the patient protection apparatus and a shorter length at the back; and
wherein the first side and second side taper at an angle from the front to the back.

2. The patient protection apparatus of claim 1 wherein the first side, second side, back, top and front visor are configured to create a hollow interior that tapers from front to back; and wherein at least one of the first side, second side, back, top and front visor are transparent.

3. The patient protection apparatus of claim 2 wherein the first side and second side extend from a height proximate ground level to a height configured to accommodate a patient platform with a patient at one of a horizontal and upwardly angled position.

4. The patient protection apparatus of claim 1 wherein each side arm aperture and back arm apertures is located within an upper third of the patient protection apparatus.

5. The patient protection apparatus of claim 1 wherein each side and back panel combined is configured to accommodate a caretaker administering patient services utilizing one side arm aperture and one back arm aperture; and wherein the plurality of back arm apertures is configured to accommodate a caretaker administering patient services utilizing two back arm apertures; and wherein the apparatus is configured to accommodate a single caretaker utilizing a side arm aperture and back arm aperture simultaneously or two back arm apertures simultaneously; and wherein the apparatus is configured to accommodate a plurality of caretakers utilizing at least one respective side arm aperture and one respective back arm aperture simultaneously.

6. The patient protection apparatus of claim 1 further including a front enclosure removably engaged to a plurality of top attachment members and side attachment members; and wherein the front enclosure is configured to extend downward from the top to a patient lap edge; and wherein the front enclosure includes a pair of enclosure overhangs configured to extend downward and around a patient platform; and wherein the apparatus further includes a removably engaged tinted shield; and wherein the tinted shield may be removably engaged via at least one of top pegs fixedly attached to the top configured to accommodate corresponding holes in the tinted shield, hook and loop fasteners on the apparatus and the tinted shield, and oppositely charged magnets fixedly attached to the tinted shield and the apparatus.

7. The patient protection apparatus of claim 6 further including a removably attached bottom front enclosure extending from the first side across the front of the apparatus to the second side of the apparatus and removably attached to each respective side via side attachment members.

8. A patient protection apparatus comprising
a first side and second side each comprising at least one of a side arm aperture, an instrument aperture, an air filter interface and a bottom securement member,
a back panel comprising a plurality of back arm apertures and at least one instrument aperture,
a top, and
a front visor,
wherein the top has a wider length at a front of the patient protection apparatus and a shorter length at a back;
wherein the first side and second side taper at an angle from the front to the back; and
wherein the patient protection apparatus is configured to removably engage a top surface of a patient platform.

9. The patient protection apparatus of claim 8 further including a width configured to be smaller than a patient platform width; and further including a length configured to extend from a position proximate a patient platform end to a position proximate a patient's upper torso; and wherein the apparatus is configured to fit overtop of a patient's upper torso when the patient is laying on a patient platform.

10. The patient protection apparatus of claim 8 wherein the front visor comprises an arcuate bottom edge and a curved interface with the top; and wherein the first side and second side each have a curved interface with the top, back panel, and front visor; and wherein the apparatus further includes a removably engaged tinted shield; and wherein the tinted shield may be removably engaged via at least one of top pegs fixedly attached to the top configured to accommodate corresponding holes in the tinted shield, hook and loop fasteners on the apparatus and the tinted shield, and oppositely charged magnets fixedly attached to the tinted shield and the apparatus.

11. The patient protection apparatus of claim 8 wherein the plurality of back arm apertures is two back arm apertures, and a back instrument aperture is positioned in between and below the two back arm apertures; and wherein each instrument apertures is positioned closer to the front than each side arm apertures; and wherein filter interfaces are positioned proximate a bottom front corner of the first side and second side respectively.

12. The patient protection apparatus of claim 8 wherein the securement members is at least one of a bottom gasket, hook and loop fasteners on a bottom surface of the apparatus configured to engage corresponding hook and loop fasteners on a top surface of the patient platform, and further including removably engaged adjustable straps each removably secured to a device bottom lip at one end and an opposing end of the adjustable strap.

13. The patient protection apparatus of claim 8 wherein each arm aperture and each instrument aperture has a self-sealing medial passthrough surrounded by at least one of rubber and silicone configured to close the passthrough when not penetrated by a respective arm and instrument.

14. The patient protection apparatus of claim 8 further including a top front enclosure removably engaged to the top that extends to a patient torso edge configured to enclose a patient's upper torso within an apparatus hollow interior.

15. A patient protection apparatus comprising
a first side and second side each comprising at least one of a side arm aperture, an instrument aperture, an air filter interface and a bottom securement member,
a back panel comprising a plurality of back arm apertures and at least one instrument aperture,
a top, and
a front visor,
wherein the top has a wider length at a front of the patient protection apparatus and a shorter length at a back;
wherein the first side and second side taper at an angle from the front to the back;
wherein the patient protection apparatus is configured to fit on top of a patient platform;
wherein the first side, second side, back panel, top and front visor are configured to create a hollow interior that tapers from front to back;
wherein the apparatus is configured to accommodate at least one caretaker administering patient services utilizing one side arm aperture and one back arm aperture; and wherein the plurality of back arm apertures is configured to accommodate at least one caretaker administering patient services utilizing two back arm apertures of the plurality of back arm apertures;
and wherein the apparatus is configured to accommodate a single caretaker utilizing a side arm aperture and back arm aperture simultaneously or two back arm apertures simultaneously;
and wherein the apparatus is configured to accommodate a plurality of caretakers utilizing at least one respective side arm aperture and one respective back arm aperture simultaneously; wherein a width of the apparatus is configured to be smaller than a patient platform width; and wherein a length of the apparatus is configured to extend from a position proximate a patient platform end to a position proximate a patient's upper torso; and wherein the apparatus is configured to fit overtop of a patient's upper torso when the patient is laying on a patient platform;
wherein the front visor comprises an arcuate bottom edge and a curved interface with the top; and wherein the first side and second side each have a curved interface with the top, back panel, and front visor; and
wherein each arm aperture and each instrument apertures has a self-sealing medial passthrough surrounded by at least one of rubber and silicone configured to close the passthrough when not penetrated by a respective arm and instrument.

16. The patient protection apparatus of claim 15 wherein the hollow interior further includes an adjustable light; and wherein the adjustable light is one of fixedly attached to a hollow interior top, removably attached to an apparatus interior side by way of a holding device, and removably attached to the apparatus via a magnet at a light base and an opposingly charged magnet on the apparatus.

17. The patient protection apparatus of claim 15 wherein a filter interface includes an interface plate with inside threading configured to accommodate a cap overtop and outside threading configured to accommodate a plug; and wherein a cap and plug are configured to close the interface when not in use; and wherein the interface plate inside threading is configured to removably attach an adapter structured to accommodate a hose therein.

18. The patient protection apparatus of claim 15 further including an upper arm mount configured to removably attach a repositionable arm operable to position the apparatus onto and off of a patient platform.

19. The patient protection apparatus of claim 18 wherein the repositionable arm is configured to attach to a dental light arm; and wherein the repositionable arm further includes at least one of a shield attachment member and tinted shield configured to adjustably screen a caretaker's eyes from reflected light.

20. The patient protection apparatus of claim 18 wherein the repositionable arm is a self-supported freestanding structure.

\* \* \* \* \*